(12) United States Patent
Blott et al.

(10) Patent No.: US 8,162,909 B2
(45) Date of Patent: Apr. 24, 2012

(54) NEGATIVE PRESSURE WOUND TREATMENT

(75) Inventors: Patrick Lewis Blott, York (GB); Bryan Greener, York (GB); Edward Yerbury Hartwell, Hull (GB); Julian Lee-Webb, York (GB); Derek Nicolini, Brough (GB)

(73) Assignee: Smith & Nephew PLC, London (GB)

( * ) Notice: Subject to any disclaimer, the term of this patent is extended or adjusted under 35 U.S.C. 154(b) by 838 days.

(21) Appl. No.: 12/066,585

(22) PCT Filed: Sep. 15, 2006

(86) PCT No.: PCT/GB2006/003416
§ 371 (c)(1),
(2), (4) Date: Sep. 29, 2008

(87) PCT Pub. No.: WO2007/031757
PCT Pub. Date: Mar. 22, 2007

(65) Prior Publication Data
US 2009/0204084 A1    Aug. 13, 2009

(30) Foreign Application Priority Data
Sep. 15, 2005   (GB) .................................. 0518804.0

(51) Int. Cl.
*A61M 1/00* (2006.01)
*A61M 1/30* (2006.01)
*A61M 31/00* (2006.01)
(52) U.S. Cl. .............. 604/319; 604/19; 604/35; 604/48; 604/317

(58) Field of Classification Search .................... 604/20, 604/289, 304–308
See application file for complete search history.

(56) References Cited

U.S. PATENT DOCUMENTS

| | | |
|---|---|---|
| 2,280,915 A | 4/1941 | Johnson |
| 3,624,821 A | 11/1971 | Henderson |
| 3,874,387 A | 4/1975 | Barbieri |
| 3,993,080 A | 11/1976 | Loseff |
| 4,112,947 A | 9/1978 | Nehring |
| 4,136,696 A | 1/1979 | Nehring |
| 4,178,938 A | 12/1979 | Au |
| 4,180,074 A | 12/1979 | Murry et al. |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |

(Continued)

FOREIGN PATENT DOCUMENTS

CA    2 369 024    10/2001

(Continued)

OTHER PUBLICATIONS

Bevan, Damon et al. Diverse and potent activities of HGF/SF in skin wound repair. J Pathol 2004: 203: 831-838.*

(Continued)

*Primary Examiner* — Leslie Deak
*Assistant Examiner* — Xin Xie
(74) *Attorney, Agent, or Firm* — Knobbe, Martens, Olson & Bear LLP

(57) ABSTRACT

An apparatus for aspirating, irrigating and/or cleansing wounds (1) using cells or tissues to cleanse the circulating fluid to enhance wound healing by destroying or limiting the harmful substances in the circulating fluid from the wound (5) thus enhancing the beneficial substances.

44 Claims, 24 Drawing Sheets

U.S. PATENT DOCUMENTS

| | | | |
|---|---|---|---|
| 4,465,485 A | 8/1984 | Kashmer et al. |
| 4,573,965 A | 3/1986 | Russo |
| 4,778,446 A | 10/1988 | Jensen |
| 4,792,328 A | 12/1988 | Beck et al. |
| 4,921,488 A | 5/1990 | Maitz et al. |
| 4,936,834 A | 6/1990 | Beck et al. |
| 4,969,880 A | 11/1990 | Zamierowski |
| 5,055,198 A | 10/1991 | Shettigar |
| 5,073,172 A | 12/1991 | Fell |
| 5,100,396 A | 3/1992 | Zamierowski |
| 5,152,757 A | 10/1992 | Eriksson |
| 5,176,663 A | 1/1993 | Svedman et al. |
| 5,261,893 A | 11/1993 | Zamierowski |
| 5,328,614 A | 7/1994 | Matsumura |
| 5,358,494 A | 10/1994 | Svedman |
| 5,360,398 A | 11/1994 | Grieshaber et al. |
| 5,380,280 A | 1/1995 | Peterson |
| 5,487,889 A | 1/1996 | Eckert et al. |
| 5,498,338 A | 3/1996 | Kruger et al. |
| 5,549,584 A | 8/1996 | Gross |
| 5,636,643 A | 6/1997 | Argenta et al. |
| 5,645,081 A | 7/1997 | Argenta et al. |
| 5,676,650 A | 10/1997 | Grieshaber et al. |
| 5,678,564 A | 10/1997 | Lawrence et al. |
| 5,716,411 A | 2/1998 | Orgill et al. |
| 5,759,570 A | 6/1998 | Arnold |
| 5,830,176 A | 11/1998 | Mackool |
| 5,911,222 A | 6/1999 | Lawrence et al. |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,626,827 B1 | 9/2003 | Felix et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 7,077,832 B2 | 7/2006 | Fleischmann |
| 7,108,683 B2 | 9/2006 | Zamierowski |
| 7,195,624 B2 | 3/2007 | Lockwood |
| 7,216,651 B2 | 5/2007 | Argenta et al. |
| 7,361,184 B2 | 4/2008 | Joshi |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,927 B2 | 5/2009 | Lockwood |
| 7,611,500 B1 | 11/2009 | Lina et al. |
| 7,625,362 B2 | 12/2009 | Boehringer et al. |
| 7,753,894 B2 | 7/2010 | Blott et al. |
| 7,759,538 B2 | 7/2010 | Fleischmann |
| 7,794,450 B2 | 9/2010 | Blott et al. |
| 7,828,782 B2 | 11/2010 | Suzuki |
| 7,862,718 B2 | 1/2011 | Doyen et al. |
| 7,879,605 B2 | 2/2011 | Rolland et al. |
| 7,964,766 B2 | 6/2011 | Blott et al. |
| 2001/0034499 A1 | 10/2001 | Sessions et al. |
| 2002/0068913 A1 | 6/2002 | Fleischmann |
| 2002/0114847 A1 | 8/2002 | Peshoff |
| 2002/0161346 A1 | 10/2002 | Lockwood et al. |
| 2003/0021775 A1 | 1/2003 | Freeman |
| 2003/0050594 A1 | 3/2003 | Zamierowski |
| 2003/0108587 A1 | 6/2003 | Orgill et al. |
| 2003/0134332 A1 | 7/2003 | Boykin |
| 2003/0144619 A1 | 7/2003 | Augustine |
| 2003/0148959 A1 | 8/2003 | Quirk et al. |
| 2003/0171675 A1 | 9/2003 | Rosenberg |
| 2003/0225347 A1 | 12/2003 | Argenta et al. |
| 2004/0054338 A1 | 3/2004 | Bybordi et al. |
| 2005/0090787 A1 | 4/2005 | Risk et al. |
| 2005/0261643 A1 | 11/2005 | Bybordi et al. |
| 2006/0029675 A1 | 2/2006 | Ginther |
| 2006/0155260 A1 | 7/2006 | Blott et al. |
| 2007/0014837 A1 | 1/2007 | Johnson et al. |
| 2007/0021698 A1 | 1/2007 | Fleischmann |
| 2007/0038172 A1 | 2/2007 | Zamierowski |
| 2007/0066945 A1 | 3/2007 | Martin |
| 2007/0129707 A1 | 6/2007 | Blott et al. |
| 2007/0141128 A1 | 6/2007 | Blott et al. |
| 2007/0167926 A1 | 7/2007 | Blott et al. |
| 2007/0219471 A1 | 9/2007 | Johnson et al. |
| 2007/0292488 A1 | 12/2007 | Bassirie et al. |
| 2007/0293830 A1 | 12/2007 | Martin |
| 2008/0033330 A1 | 2/2008 | Moore |
| 2008/0069855 A1 | 3/2008 | Bonutti |
| 2008/0091133 A1 | 4/2008 | Matter |
| 2008/0125697 A1 | 5/2008 | Gao |
| 2008/0125698 A1 | 5/2008 | Gerg et al. |
| 2008/0199513 A1 | 8/2008 | Beretta et al. |
| 2009/0012483 A1 | 1/2009 | Blott et al. |
| 2009/0054855 A1 | 2/2009 | Blott et al. |
| 2009/0069759 A1 | 3/2009 | Blott et al. |
| 2009/0143753 A1 | 6/2009 | Blott et al. |
| 2009/0221977 A1 | 9/2009 | Blott et al. |
| 2009/0254054 A1 | 10/2009 | Blott et al. |
| 2009/0306580 A1 | 12/2009 | Blott et al. |
| 2009/0306609 A1 | 12/2009 | Blott et al. |
| 2009/0312723 A1 | 12/2009 | Blott et al. |
| 2010/0100075 A1 | 4/2010 | Weston et al. |
| 2010/0274167 A1 | 10/2010 | Martin et al. |
| 2010/0297208 A1 | 11/2010 | Fry et al. |
| 2011/0004171 A1 | 1/2011 | Blott et al. |
| 2011/0009835 A1 | 1/2011 | Blott et al. |
| 2011/0213319 A1 | 9/2011 | Blott et al. |
| 2011/0213320 A1 | 9/2011 | Blott et al. |

FOREIGN PATENT DOCUMENTS

| | | |
|---|---|---|
| DE | 3935818 A1 | 5/1991 |
| DE | 40 12 232 A1 | 10/1991 |
| DE | 41 02 684 A1 | 8/1992 |
| DE | 198 44 355 | 4/2000 |
| EP | 0020662 B1 | 7/1984 |
| EP | 0853950 B1 | 8/1995 |
| EP | 0880953 B1 | 5/1998 |
| EP | 0777504 B1 | 10/1998 |
| FR | 1 163 907 | 10/1958 |
| GB | 114754 | 4/1918 |
| GB | 641061 | 8/1950 |
| GB | 1 224 009 A | 3/1971 |
| GB | 1549756 A | 8/1979 |
| GB | 2195255 A | 4/1988 |
| GB | 2378392 A | 2/2003 |
| JP | S62-279885 | 12/1987 |
| JP | 2001314479 A | 11/2001 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 93/09727 | 5/1993 |
| WO | WO 94/03214 | 2/1994 |
| WO | WO 9420041 A1 * | 9/1994 |
| WO | WO 98/13000 | 4/1998 |
| WO | WO 00/07653 | 2/2000 |
| WO | WO 00/50143 A | 8/2000 |
| WO | WO 01/37773 A1 | 5/2001 |
| WO | WO 02/083046 A1 | 10/2002 |
| WO | WO 02/092783 | 11/2002 |
| WO | WO 02/092783 A2 | 11/2002 |
| WO | WO 03/101385 | 11/2003 |
| WO | WO 03/101508 | 12/2003 |
| WO | WO 2004/024300 | 3/2004 |
| WO | WO 2004/037334 | 5/2004 |
| WO | WO 2004037334 A1 * | 5/2004 |
| WO | WO 2005/046760 | 5/2005 |
| WO | WO 2005/046762 | 5/2005 |
| WO | WO 2005046762 A1 * | 5/2005 |
| WO | WO 2005/051461 | 6/2005 |
| WO | WO 2005/070480 | 8/2005 |
| WO | WO 2005/082435 | 9/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2006/052745 | 5/2006 |

| WO | WO 2006/054323 | 5/2006 |
| --- | --- | --- |
| WO | WO 2006/114638 | 11/2006 |
| WO | WO 2007/013064 | 2/2007 |
| WO | WO 2007/019038 | 2/2007 |
| WO | WO 2008/005532 A2 | 1/2008 |
| WO | WO 2008/005532 A3 | 1/2008 |
| WO | WO 2008/005996 | 1/2008 |
| WO | WO 2008/008032 | 1/2008 |
| WO | WO 2008/010094 | 1/2008 |
| WO | WO 2008/028975 | 3/2008 |
| WO | WO 2008/030872 | 3/2008 |
| WO | WO 2008/036360 | 3/2008 |
| WO | WO 2008/039314 | 4/2008 |
| WO | WO 2008/040020 | 4/2008 |
| WO | WO 2008/041926 | 4/2008 |
| WO | WO 2008/048481 | 4/2008 |
| WO | WO 2009/158126 | 12/2009 |

OTHER PUBLICATIONS

Mitchell, Richard et al. Pocket Companion to Robbins and Cotran Pathologic Basis of Disease, 7$^{th}$ edition, 2006, p. 55.*
U.S. Appl. No. 10/599,722, filed Oct. 6, 2006, Blott et al.
U.S. Appl. No. 10/599,725, filed Oct. 6, 2006, Blott et al.
U.S. Appl. No. 10/599,728, filed Oct. 6, 2006, Blott et al.
U.S. Appl. No. 11/919,354, filed Oct. 26, 2007, Blott et al.
U.S. Appl. No. 11/919,355, filed Oct. 26, 2007, Blott et al.
U.S. Appl. No. 11/919,369, filed Oct. 26, 2007, Blott et al.
U.S. Appl. No. 11/957,860, filed Dec. 17, 2007, Blott et al.
U.S. Appl. No. 12/066,578, filed Mar. 12, 2008, Blott et al.
U.S. Appl. No. 12/066,730, filed Mar. 13, 2008, Blott et al.
U.S. Appl. No. 12/094,963, filed May 23, 2008, Dagger.
Aubrey, D.A., et al., Treatment of the Perineal Wound after Proctectomy by Intermittent Irrigation, Arch. Surg., Oct. 1984, 119, pp. 1141-1144.
Chariker, M.E., et al, Effective Management of Incisional and Cutaneous Fistulae with Closed Suction Wound Drainage, Contemporary Surgery. Jun. 1989, vol. 34 USA, pp. 59-63.
Dilmaghani et al., A Method for Closed Irrigation and Suction Therapy in Deep Wound Infections, Journal of Bone and Joint Surgery, 1969, vol. 51-A, No. 2, pp. 323-342.
Hartz, R.S., et al., Healing of the Perineal Wound, Arch. Surg., Apr. 1980, 115, 471-474.
International Search Report for International Application No. PCT/GB2006/003416 date of mailing Nov. 30, 2006 in 4 pages.
International Preliminary Report for International Application No. PCT/GB2006/003416, Date of Report Issuance Mar. 18, 2008, in 11 pages.
Svedman, P., Irrigation Treatment in Split-Thickness Skin Grafting of Intractable Leg Ulcers; Scand J. Plast. Reconst. Surg., 1985, 19, pp. 211-213.
Svedman, P., Irrigation Treatment of Leg Ulcers, The Lancet, Sep. 1983, pp. 532-534.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., A Dressing System Providing Fluid Supply and Suction Drainage Used for Continuous or Intermittent irrigation, Annals of Plastic Surgery, vol. 17, No. 2, Aug. 1986, pp. 125-133.
Swift, et al, Quorum Sensing in *Aeromonas hydrophila* and *Aeromonas salmoncida*: Identification of LuxRI Homologs AhyRI and AsaRI and Their Cognate N-Acylhomoserine Lactone Signal Molecules, J. Bacteriol., 1997, 179(17):5271-5281.
Teder and Svedman et al., Continuous Wound Irrigation in the Pig, Journal of Investigative Surgery, 1990, vol. 3, pp. 399-407.
Wound Suction, Nursing, Oct., 1975, USA, pp. 52-53.
Urschel, J.D., et al., The Effect of Mechanical Stress on Soft and Hard Tissue Repair; A Review, Br. Journ. Plast. Surg., 1988, 41, 182-186.
Vijanto, J. and J. Raekallio, Local Hyperalimentation of Open Wounds, Br. J. surg., 1976, 63, pp. 427-430.
Westaby, S., et al., A Wound Irrigation Device, The Lancet, Sep. 2, 1978, pp. 503-504.
Wooding-Scott, Margaret, et al., No Wound is Too Big for Resourceful Nurses, RN, USA, Dec. 1988, pp. 22-25.
U.S. Appl. No. 12/300,636, filed Nov. 12, 2008, Fry et al.
Tribble, David E. M.D., "An Improved Sump Drain-Irrigation Device of Simple Construction," Archives of Surgery, New York, 1972, vol. 105, pp. 511-513.
U.S. Appl. No. 10/576,263, filed Nov. 9, 2006, published as 2007/0141128 and its ongoing prosecution history including without limitation Office Actions, Amendments, Remarks, and any other potentially relevant documents.
U.S. Appl. No. 10/599,728, filed Nov. 3, 2008, published as 2009/0054855 and its ongoing prosecution history including without limitation Office Actions, Amendments, Remarks, and any other potentially relevant documents.
U.S. Appl. No. 10/599,725, filed Sep. 22, 2008, published as 2009/0069759 and its ongoing prosecution history including without limitation Office Actions, Amendments, Remarks, and any other potentially relevant documents.
U.S. Appl. No. 12/066,730, filed Oct. 9, 2008, published as 2009/0143753 and its ongoing prosecution history including without limitation Office Actions, Amendments, Remarks, and any other potentially relevant documents.
U.S. Appl. No. 12/066,578, filed Oct. 10, 2008, published as 2009/0221977 and its ongoing prosecution history including without limitation Office Actions, Amendments, Remarks, and any other potentially relevant documents.
U.S. Appl. No. 12/416,829, filed Apr. 1, 2009, published as 2009/0254054 and its ongoing prosecution history including without limitation Office Actions, Amendments, Remarks, and any other potentially relevant documents.
U.S. Appl. No. 11/919,354, filed Oct. 26, 2007, published as 2009/0306580 and its ongoing prosecution history including without limitation Office Actions, Amendments, Remarks, and any other potentially relevant documents.
U.S. Appl. No. 11/919,355, filed Oct. 26, 2007, published as 2009/0306609 and its ongoing prosecution history including without limitation Office Actions, Amendments, Remarks, and any other potentially relevant documents.
U.S. Appl. No. 11/919,369, filed Oct. 26, 2007, published as 2009/0312723 and its ongoing prosecution history including without limitation Office Actions, Amendments, Remarks, and any other potentially relevant documents.
U.S. Appl. No. 12/445,043, filed Apr. 9, 2009, published as 2010/0100075 and its ongoing prosecution history including without limitation Office Actions, Amendments, Remarks, and any other potentially relevant documents.
U.S. Appl. No. 12/762,250, filed Apr. 16, 2010 and its ongoing prosecution history including without limitation Office Actions, Amendments, Remarks, and any other potentially relevant documents.
U.S. Appl. No. 12/832,002, filed Jul. 7, 2010 and its ongoing prosecution history including without limitation Office Actions, Amendments, Remarks, and any other potentially relevant documents.
U.S. Appl. No. 12/832,032, filed Jul. 7, 2010 and its ongoing prosecution history including without limitation Office Actions, Amendments, Remarks, and any other potentially relevant documents.
U.S. Appl. No. 12/976,949, filed Dec. 22, 2010, published as 2011/0213319 and its ongoing prosecution history including without limitation Office Actions, Amendments, Remarks, and any other potentially relevant documents.
U.S. Appl. No. 12/976,935, filed Dec. 22, 2010, published as 2011/0213320 and its ongoing prosecution history including without limitation Office Actions, Amendments, Remarks, and any other potentially relevant documents.
U.S. Appl. No. 13/213,491, filed Aug. 19, 2011, and its ongoing prosecution history including without limitation Office Actions, Amendments, Remarks, and any other potentially relevant documents.
U.S. Appl. No. 10/599,722, filed Sep. 19, 2008, published as 2009/0012483 and its ongoing prosecution history including without limitation Office Actions, Amendments, Remarks, and any other potentially relevant documents.

U.S. Appl. No. 12/300,636, filed Sep. 29, 2009, published as 2010/0297208 and its ongoing prosecution history including without limitation Office Actions, Amendments, Remarks, and any other potentially relevant documents.

Achterberg, V., Ph.D., Hydroactive dressings and serum proteins: an in vitro study, Journal of Wound Care, Feb. 1996, vol. 5, No. 2, (pp. 79-82).

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Morykwas, M. J., et al.: "Nonsurgical Modalities to Enhance Healing and Care of Soft Tissue Wounds", Journal of the Southern Orthopaedic Association, vol. 6, No. 4 Winter 1997 in 12 pages.

Nursing75, "Wound Suction", Nursing, USA, pp. 52-53.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Stewart, Joanne, Ph.D., World Wide Wounds—Next generation of products for wound management—2002 (13 pages).

European Patent Office; International Search Report of related PCT application, application No. PCT/GB2006/003416; mailing date Nov. 30, 2006.

European Patent Office; International Preliminary Report on Patentability and Written Opinion of related PCT application, application No. PCT/GB2006/003416; mailing date Mar. 18, 2008.

* cited by examiner

Section Through X-X

Section Through X-X

Section Through X-X

Section Through X-X

Section Through X-X

Section Through X-X

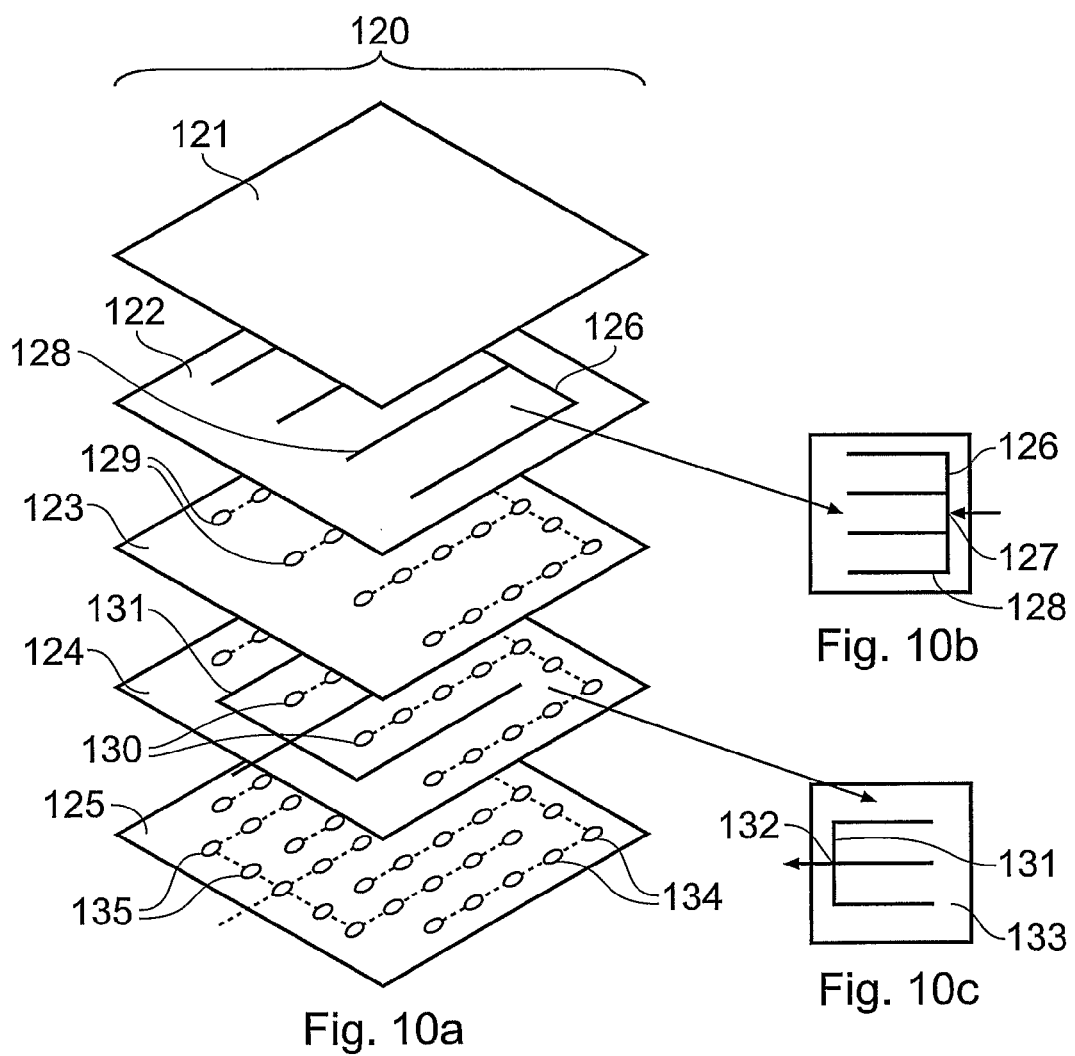

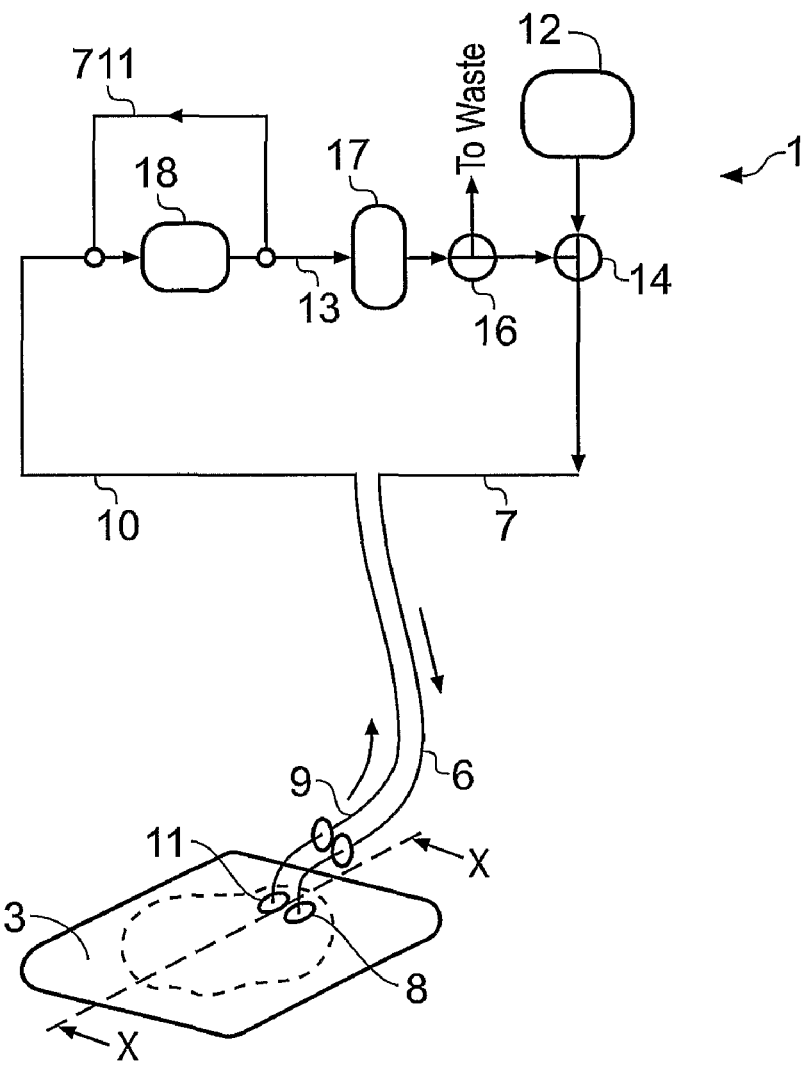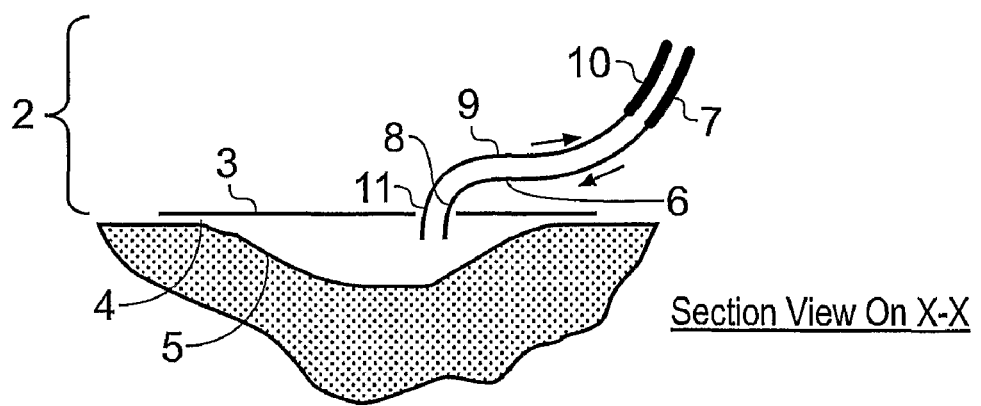
Fig. 11

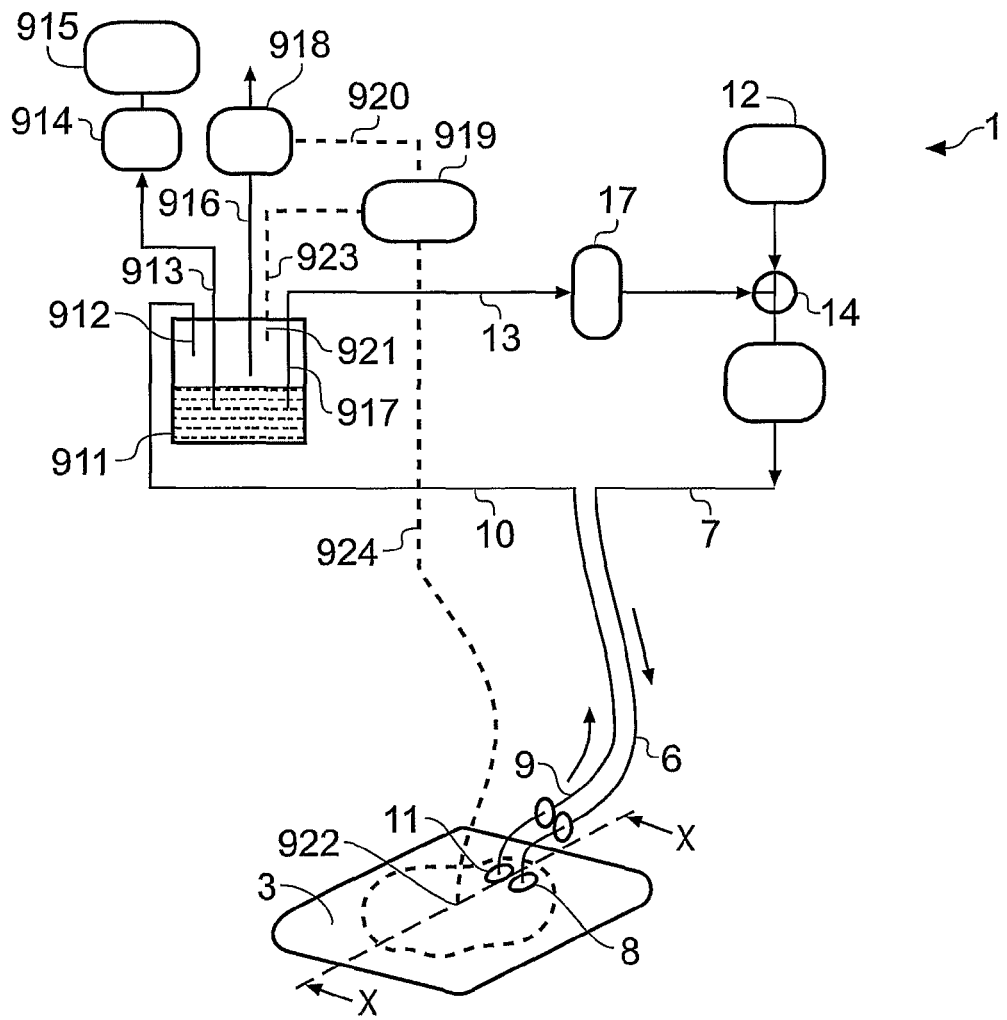
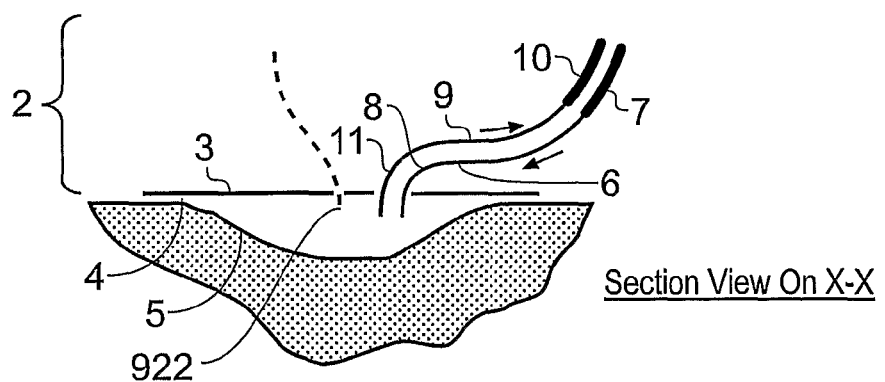
Fig. 27

Schematic representation Exudialysis flow system

NEGATIVE PRESSURE WOUND TREATMENT

CROSS REFERENCE TO RELATED APPLICATIONS

This application is the United States national phase of International Application No. PCT/GB2006/003416 filed on Sep. 15, 2006 and published in English on Mar. 22, 2007 as International Publication No. WO 2007/031757 A1, which application claims priority to Great Britain Patent Application No. 0518804.4 filed on Sep. 15, 2005, the entire contents of both of which are incorporated herein by reference.

The present invention relates to apparatus and a medical wound dressing for aspirating, irrigating and/or cleansing wounds using cells or tissue, and a method of treating wounds using such apparatus for aspirating, irrigating and/or cleansing wounds using cells or tissue.

It relates in particular to such an apparatus, wound dressing and method that can be easily applied to a wide variety of, but in particular chronic, wounds, to cleanse them of materials that are deleterious to wound healing, whilst retaining and/or adding materials that are beneficial in some therapeutic aspect, in particular to wound healing.

Before the present invention, aspirating and/or irrigating apparatus therefor were known, and tended to be used to remove wound exudate during wound therapy. In known forms of such wound therapy, the offtake from the wound, especially when in a highly exuding state, is voided to waste, e.g. to a collection bag.

Materials deleterious to wound healing are removed in this way.

However, materials that are beneficial in promoting wound healing, such as growth factors, cell matrix components, and other physiologically active components of the exudate from a wound are lost to the site where they can be potentially of most benefit, i.e. the wound bed, when such therapy is applied.

Such known forms of wound dressing and aspiration and/or irrigation therapy systems often create a wound environment under the dressing that thus may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

It thus would be desirable to provide a system of therapy which can remove materials deleterious to wound healing from wound exudate, whilst retaining and/or adding materials that are beneficial in promoting wound healing in contact with the wound bed.

Dialysis is a known method of treating bodily fluids such as blood ex vivo, to cleanse them of materials that are deleterious to the body systemically. Removal of such materials by contact with the dialysate is the prime purpose of dialysis, whilst also retaining and/or adding materials such as blood, cells and proteins. Other materials that may have an additional positive therapeutic action are potentially lost to the system through the dialysis membrane, which is also permeable to them. The balance of such materials in the bodily fluid in recirculation may thus be further depleted.

It would be desirable to provide a system of therapy which can remove materials deleterious to wound healing from wound exudate, without substantially diluting materials that are beneficial in promoting wound healing in contact with the wound bed, and which can continuously supply and recirculate such materials to the wound simultaneously.

Dialysis for treating bodily fluids is also a systemic therapy, since the treated fluid is returned to within the body. This is in contrast to a topical therapy in which the treated fluid is recycled outside the body, e.g. to a wound.

Most dialysis also requires large amounts of bodily fluids such as blood, and consequently the relevant devices tend not to be portable.

Even when in a highly exuding state, chronic wounds produce relatively little fluid to be treated compared with internal bodily systems and relatively little materials that are beneficial in some therapeutic aspect to be retained in and/or added to the wound and/or its environment.

Before the present invention, known forms of apparatus for cleansing bodily fluids such as blood of deleterious materials, such as dialysis units or filtration devices, comprised a means for fluid cleansing that is respectively a two- or single-phase system.

In such apparatus the circulating fluid from the body passes through the means for fluid cleansing and materials deleterious to wound healing are removed.

For example, respectively such materials as solutes or disperse phase species pass into the dialysate through a dialysis membrane, or as particulates, e.g. cell debris and microorganisms, are removed by one or more macroscopic and/or microscopic filters that allow materials that are beneficial in some therapeutic aspect to pass.

It would be desirable to provide a system of therapy which can remove materials deleterious to wound healing from wound exudate, while being able to supply materials that are beneficial to wound healing.

We have found that cells or tissue may be used to particular advantage for these purposes in the wound healing process. Means for fluid cleansing may use cells or tissue for cleansing exudate. Additionally, it may supply growth factors, cell matrix components, biological signalling molecules involved in wound healing and other physiologically active components to the wound, where they can be potentially of most benefit.

It is an object of the present invention
a) to obviate at least some of the abovementioned disadvantages of known aspiration and/or irrigation therapy systems, and
b) to provide a system of therapy which can remove materials deleterious to wound healing from wound exudate, whilst retaining and/or adding materials that are beneficial in promoting wound healing in contact with the wound bed.

It is a further object of the present invention
a) to obviate at least some of the abovementioned disadvantages of known dialysis systems, and
b) to provide a system of therapy which can remove materials deleterious to wound healing from wound exudate, whilst retaining and/or adding materials that are beneficial in promoting wound healing in contact with the wound bed,
c) without affecting the body systemically.

It is a yet further object of the present invention
a) to obviate at least some of the abovementioned disadvantages of known dialysis systems, and
b) to provide a system of therapy which can remove materials deleterious to wound healing from wound exudate, whilst retaining and/or adding materials that are beneficial in promoting wound healing in contact with the wound bed, and
c) is portable.

Vascular supply to, and circulation in, tissue underlying and surrounding the wound is often compromised. It is a further object of the present invention to provide a system of therapy that retains and supplies therapeutically active amounts of materials that are beneficial in reversing this effect whilst removing deleterious materials, thereby promoting wound healing.

Thus, according to a first aspect of the present invention there is provided an apparatus for aspirating, irrigating and/or cleansing wounds using cells or tissue, characterised in that it comprises
a) a fluid flow path, comprising
   i) a conformable wound dressing, having
      a backing layer which is capable of forming a relatively fluid-tight seal or closure over a wound and
      at least one inlet pipe for connection to a fluid supply tube, which passes through and/or under the wound-facing face, and
      and at least one outlet pipe for connection to a fluid offtake tube, which passes through and/or under the wound-facing face,
      the point at which the or each inlet pipe and the or each outlet pipe passes through and/or under the wound-facing face forming a relatively fluid-tight seal or closure over the wound,
      at least one inlet pipe being connected to a fluid recirculation tube, and at least one outlet pipe being connected to a fluid offtake tube: and
   ii) a means for fluid cleansing using cells or tissue having at least one inlet port connected to a fluid offtake tube and at least one outlet port connected to a fluid recirculation tube;
b) a fluid reservoir connected by a second fluid supply tube to an integer of the flow path (optionally or as necessary via means for flow switching between supply and recirculation);
c) a device for moving fluid through the wound dressing and means for fluid cleansing using cells or tissue, and optionally or as necessary the fluid supply tube; and
d) optionally means for bleeding the flowpath,
such that fluid may be supplied to fill the flowpath from the fluid reservoir via the fluid supply tube (optionally or as necessary via the means for flow switching) and recirculated by the device through the flow path.

According to the present invention there is provided an apparatus for aspirating, irrigating and/or cleansing wounds using cells or tissue, characterised in that is comprises
a) a fluid flow path, comprising
   i) a wound dressing, having
      a backing layer and
      at least one inlet pipe for connection to a fluid supply tube, which passes through and/or under the backing layer, and
      at least one outlet pipe for connection to a fluid offtake tube, which passes through and/or under the backing layer,
      at least one inlet pipe being connected to a fluid recirculation tube, and at least one outlet pipe being connected to a fluid offtake tube; and
   ii) a means for fluid cleansing using cells or tissue having at least one inlet port connected to a fluid offtake tube and at least one outlet port connected to a fluid recirculation tube;
b) a fluid reservoir connected by a second fluid supply tube to an integer of the flow path (optionally or as necessary via means for flow switching between supply and recirculation);
c) a device for moving fluid through the wound dressing and means for fluid cleansing using cells or tissue, and optionally or as necessary the fluid supply tube; and
d) optionally means for bleeding the flowpath,
such that fluid may be supplied to fill the flowpath from the fluid reservoir via the fluid supply tube (optionally or as necessary via the means for flow switching) and recirculated by the device through the flow path.

According to another aspect, there is provided an apparatus for aspirating, irrigating and/or cleansing wounds using cells or tissue, characterised in that it comprises
a) a fluid flow path, comprising
   i) a wound dressing, having a backing layer and at least one inlet pipe for connection to a fluid supply tube, which passes through and/or under the backing layer, and at least one outlet pipe for connection to a fluid offtake tube, which passes through and/or under the backing layer, at least one inlet pipe being connected to a fluid recirculation tube, and at least one outlet pipe being connected to a fluid offtake tube: and
   ii) a means for fluid cleansing using cells or tissue having at least one inlet port connected to a fluid offtake tube and at least one outlet port connected to a fluid recirculation tube;
b) a fluid reservoir connected by a second fluid supply tube to an integer of the flow path (optionally or as necessary via means for flow switching between supply and recirculation);
c) a device for moving fluid through the wound dressing and means for fluid cleansing using cells or tissue, and optionally or as necessary the fluid supply tube; and
d) optionally means for bleeding the flowpath, such that fluid may be supplied to fill the flowpath from the fluid reservoir via the fluid supply tube (optionally or as necessary via the means for flow switching) and recirculated by the device through the flow path.

There is also provided herein the aspect disclosed above wherein the flow rate is a varied flow rate, either randomly or regularly cyclical. Further, provided herein is the aspect disclosed above wherein the regular or random cycles of flow rate have a frequency of up to 48 per 24 hours, and/or wherein the pulses of flow velocity have a frequency of from 1 to 60 per min. Also provided is the aspect described above wherein the aspiration and irrigation is either sequential or simultaneous.

The means for fluid cleansing uses cells or tissue for cleansing exudate. Often, it is in the form of a hollow body such as a container, e.g. a canister, cartridge or cassette, with a chamber or compartment that contains a cell or tissue component, through which the wound exudate or a mixture of wound exudate and irrigant (or modified irrigant) is passed and recirculated by the device through the flow path.

The structures noted above will often be made of glass, and/or synthetic polymeric materials. For example, such a structure may be a glass cylinder defining a chamber with axial inlet and outlet ports for throughflow, which contains cells or tissue on a scaffold.

The circuit element that contains the tissue or cell component will normally be mounted within a device constructed to maintain the viability and activity of the cells. This would include but not be limited to the means for supplying nutrition and regulating the exchange of gases and maintaining an optimum temperature.

As described in further detail hereinafter, the means for fluid cleansing using cells or tissue may be a single or dual phase circuit element.

The tissue component has the ability to remove elements detrimental to wound healing or to modify the cellular elements of the wound bed through biochemical, enzymatic or physical means by the elaboration or the uptake of materials or the combination of both elaboration and uptake.

The cells used in the present invention may be hepatocytes, or any other suitable cell type known in the art.

Depending on the particular type of wound being treated and the particular cells or tissue used in the present apparatus for aspirating, irrigating and/or cleansing wounds, the deleterious materials to be removed may include proteases, such as serine proteases, e.g. elastase and thrombin; cysteine proteases; matrix metalloproteases, e.g. collagenase; and carboxyl (acid) proteases;

inhibitors of angiogenesis such as thrombospondin-1 (TSP-1), Plasminogen activator inhibitor, or angiostatin (plasminogen fragment)

pro-inflammatory cytokines such as tumour necrosis factor alpha (TNF-α)

and interleukin 1 beta (IL-1β), and inflammatories, such as lipopolysaccharides, and e.g. histamine.

It may also have the ability to add elements beneficial to wound healing to the exudate and irrigant (or modified irrigant) or to modify the exudate and irrigant through biochemical, enzymatic or physical means to contain elements beneficial to wound healing, as it is passed and recirculated by the device through the flow path.

Again, depending on the particular type of wound being treated and the particular cells or tissue used in the present apparatus for aspirating, irrigating and/or cleansing wounds, the beneficial materials to be added may include antagonists to the materials deleterious to wound healing in the wound exudate, such as, for example enzymes or others, such as protease inhibitors, such as serine protease inhibitors, cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;

They further include peptides (including cytokines, e.g. bacterial cytokines, such as α-amino-γ-butyrolactone and L-homocarnosine); and other physiologically active components.

The tissue component may be an ex vivo (autologous, allogeneic or xenogenic) uncultured tissue explant. Alternatively the tissue component may be formed from separated or partially separated cells which have either been used without a period of culture or they may have been cultured in vitro. The process of culture may involve growth and proliferation or just incubation in culture. The source tissues may be tissue from any organ such as skin, muscle, bone, neural, connective tissue, intestinal, liver or amniotic tissue and other organs or combinations thereof, whose cells and tissue retain the appropriate properties.

The tissue component that provides the exudate cleansing may consist of a co-culture. A co-culture encompasses the in vitro or ex vivo culture of two or more cell types or tissue explants. This might be with one or both input cells or tissues fully viable or viable, but rendered non-dividing, through irradiation or chemical treatment. Exudate cleansing may be provided where the input cells or tissues are intimately mixed or intermingled, or they may be present as layers one on the other.

In some systems a semi permeable membrane or matrix between the component cells or tissues allows communication through biochemicals or proteins or other signals, but no cell apposition between the input cell types. In further systems conditioned medium is collected from one input cell or tissue type and given to the second input cell or type and given back to the first input cell type (sequentially or continuously) to generate the optimal cleansing actions.

The cell or tissue component may be activated either singly or repeatedly through the delivery of biochemical, protein, enzymatic or physical means or through electromagnetic irradiation, ultrasonic or electrical stimulation.

The means for fluid cleansing using cells or tissue may as desired be a 'single-phase system'.

In this, the circulating fluid from the wound and the fluid reservoir passes through a self-contained system that contains the tissue or cell component in which materials deleterious to wound healing are removed and the cleansed fluid, still containing materials from the wound that are beneficial in promoting wound healing, with added elements beneficial to wound healing to the exudate and irrigant (or modified irrigant), and/or modified through biochemical, enzymatic or physical means to contain elements beneficial to wound healing, is returned via the recirculation tube to the wound bed.

No other fluid phase is supplied, passes into such means for fluid cleansing, and is recirculated by the device through the flow path back into the wound, with the possible exception of any fluid phase necessary to maintain the viability and activity of the cells, which could include but not be limited to means for supplying nutrition and regulating the exchange of gases and maintaining an optimum temperature, and/or to maintain the desired balance of fluid in recirculation.

Alternatively, where appropriate it may be provided in the form of a two-phase system.

In this, the circulating fluid from the wound and the fluid reservoir passes through a system in which the fluid is not in contact with any cells that remove materials deleterious to wound healing, but recirculates in indirect or (less usually, direct) contact with a second fluid (dialysate) phase, more usually a liquid, which is in direct contact with the cell or tissue component that removes materials deleterious to wound healing.

The cleansed fluid, still containing materials from the wound that are beneficial in promoting wound healing, with added elements beneficial to wound healing to the exudate and irrigant (or modified irrigant), and/or modified through biochemical, enzymatic or physical means to contain elements beneficial to wound healing, is returned via the recirculation tube to the wound bed.

The first and second phases in such means for fluid cleansing are often separated by an integer which is permeable to materials deleterious to wound healing, such as a permeable or semi permeable membrane or matrix between the fluids that allows such materials to pass between the phases to and from the cell or tissue component. Such systems are described in further detail hereinafter.

Where the apparatus of the invention for aspirating, irrigating and/or cleansing using cells or tissue wounds is provided with means for fluid cleansing using cells or tissue is a single-phase system, it may be of any conventional type.

Examples of the means for fluid cleansing using cells or tissue in such a system include a hollow body such as a container, e.g. a canister, cartridge or cassette, with a chamber or compartment that contains a cell or tissue component, through which the wound exudate or a mixture with irrigant passes. For example, such a structure may be a glass cylinder defining a chamber with axial inlet and outlet ports for throughflow, which contains cells or tissue, optionally bound to a polymer film.

It may contain a cell or tissue component that is not bound to an insoluble and immobilised substrate over and/or through which the irrigant and/or wound exudate from the wound dressing passes.

It then also appropriately comprises two or more integers which are permeable to the wound exudate or a mixture with irrigant, but have apertures, holes, openings, orifices, slits or pores of sufficiently small cross-dimension to hold the cell or tissue component, and to retain particulates, e.g. cell debris, in the hollow body.

Each of the integers may then effectively form a macroscopic and/or microscopic filter.

Alternatively, it may contain a cell or tissue component that is bound to an insoluble and immobilised substrate over and/or through which the irrigant and/or wound exudate from the wound dressing passes, e.g. a scaffold. This will often be of a material that is not (cyto)toxic and is biocompatible and inert to any components that are beneficial in promoting wound healing, including natural and synthetic polymeric materials, which may typically in the form of a conformable film, sheet or membrane, often with apertures, holes, openings, orifices, slits or slots of small cross-dimension. It may then effectively form a structure which is a mesh, grid, lattice, net or web.

The means for fluid cleansing then may not need to comprises two or more integers which are permeable to the wound exudate or a mixture with irrigant to hold the cell or tissue component in the hollow body, but they may be desirable to retain particulates, e.g. cell debris.

Where the apparatus of the invention for aspirating, irrigating and/or cleansing using cells or tissue wounds is provided with means for fluid cleansing using cells or tissue is a two-phase system, it may be of any conventional type.

In examples of the means for fluid cleansing using cells or tissue that is a two-phase system, circulating fluid from the wound and the fluid reservoir is indirect or (less usually, direct) contact with a second fluid (dialysate) phase, usually a liquid, which is in direct contact with the cell or tissue component that removes materials deleterious to wound healing.

Usually it is provided in a form in which the two fluids (recirculation fluid and dialysate) are separated by a significantly two-dimensional integer, for example a polymer film, sheet or membrane or hollow fibre or filament that is permeable to materials in the circulating fluid in the apparatus.

Materials deleterious to wound healing are removed into the dialysate, and the cleansed fluid,
still containing materials from the wound that are beneficial in promoting wound healing,
with added elements beneficial to wound healing to the exudate and irrigant (or modified irrigant), and/or
modified through biochemical, enzymatic or physical means to contain elements beneficial to wound healing,
is returned via the recirculation tube to the wound bed.

In this form in which the two-phase system, such as a dialysis unit, is provided, typically in use the dialysate moves past the circulating fluid in the apparatus in a co- or preferably counter-current direction.

Pumps, such as peristaltic pumps, and/or valves control the direction of the two fluid flows.

However, the cleansing fluid, which is in direct contact with the cell or tissue component that removes materials deleterious to wound healing may less usually be static, although this may not provide a system with sufficient (dynamic) surface area to remove materials deleterious to wound healing from wound exudate at a practical rate.

Typical dialysate flow rates in a dialytic means for fluid cleansing using cells or tissue in the present apparatus for aspirating, irrigating and/or cleansing wounds using cells or tissue are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

The film, sheet or membrane may be substantially flat, and depending on any pressure differential across it may require other materials on or in it to stiffen, reinforce or otherwise strengthen it.

However, this may not provide a system with sufficient functional surface area to remove materials deleterious to wound healing from wound exudate at a practical rate.

To be suitable for use, in particular in chronic wound dialysis, with relatively high concentrations of materials that are deleterious to wound healing, it may be advantageous to provide a system in which the film, sheet or membrane of a polymeric material is in a more convoluted form.

This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid,
still containing materials from the wound that are beneficial in promoting wound healing,
with added elements beneficial to wound healing to the exudate and irrigant (or modified irrigant), and/or
modified through biochemical, enzymatic or physical means to contain elements beneficial to wound healing,
is returned via the recirculation tube to the wound.

Examples of suitable materials for the film, sheet or membrane include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly (methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The membrane should have a molecular weight cut off (MWCO) chosen to allow perfusion of species deleterious to wound healing that have been targeted for removal from the wound. For example, perfusion of the serine protease elastase (molecular weight 25900 Dalton) would require a membrane with MWCO >25900 Dalton. The MWCO threshold can be varied to suit each application between 1 and 3000000 Dalton.

It may be desired to provide a system of therapy which can remove materials deleterious to wound healing from wound exudate through cellular biochemical, enzymatic or physical means, while a) retaining the relevant antagonists, for example degrading enzymes, or sequestrating agents, on the dialysate side of the membrane,
b) supplying such materials if they are beneficial to wound healing into the exudate and irrigant (or modified irrigant), and/or
c) supplying into the exudate and irrigant (or modified irrigant) other materials that are beneficial to wound healing and
   i) are expressed by the cell or tissue component that also removes materials deleterious to wound healing, or
   ii) are added elements beneficial to wound healing.

A particular advantage of option a) in the two-phase system, is where an antagonist that removes materials deleterious to wound healing from wound exudate is (cyto)toxic or bioincompatible, or not inert to any components that are beneficial in promoting wound healing.

The system does not allow any significant amounts of antagonist to diffuse freely out of the dialysate into the irrigant fluid. The active material can however act beneficially on the fluid.

As an example of option a), the antagonist to elastase, alpha-1-antitrypsin (AAT) (molecular weight 54000 Dalton) may occur in the cell or tissue component and removes elastase (which is deleterious to wound healing). A membrane with MWCO >25900 Dalton does not allow any significant amounts of the inhibitor, which is beneficial in promoting chronic wound healing, to diffuse freely out of the dialysate and it remains there.

As an example of option b), a less conventional type of two-phase system may be used as the means for fluid cleansing using cells or tissue. In this type, the polymer film, sheet or membrane is not an integer selectively permeable to materials deleterious to wound healing. It will also permit a broad spectrum of components of the exudate from a wound and/or irrigant fluid that may be larger or smaller molecules, but are beneficially involved in wound healing to pass freely to and fro through it. Some species will pass from the dialysate to the irrigant and/or wound exudate and back.

The target materials deleterious to wound healing pass into the dialysate from the exudate through the non-selectively permeable polymer film, sheet or membrane. Unlike the other components of the exudate from a wound and/or irrigant fluid, the target materials deleterious to wound healing come into contact with the dialysate and/or the cells or tissue, optionally on an integer with at least one surface in the dialysate, and are removed by the appropriate antagonists, binders and/or degraders.

Thus, unlike the other components of the exudate from a wound and/or irrigant fluid the target materials are constantly removed from the dialysate, very little of these species will pass from the dialysate into the irrigant and/or wound exudate, and a steady state concentration equilibrium is not set up, even if the species are constantly 'topped up' from the wound dressing.

If (preferably) none of the dialysate is voided to waste, e.g. to a collection bag, a steady state concentration equilibrium of the untargeted species is eventually set up between the dialysate and the irrigant and/or wound exudate, which is 'topped up' from the wound dressing.

Circulating wound fluid aids in removal from recirculation of the materials deleterious to wound healing from wound exudate, and in the quicker attainment of this equilibrium of these materials. The cleansed fluid, still containing materials from the wound that are beneficial in promoting wound healing, with added elements beneficial to wound healing to the exudate and irrigant (or modified irrigant), and/or
modified through biochemical, enzymatic or physical means to contain elements beneficial to wound healing,
is returned to the recirculation tube and to where materials beneficial in promoting wound healing can be potentially of most benefit, i.e. the wound bed.

Specifically, a membrane with MWCO >54000 Dalton will allow significant amounts of elastase that is deleterious to chronic wound healing to diffuse freely into the dialysate and eventually to be removed by alpha-1-antitrypsin (AAT) (molecular weight 54000 Dalton) that may occur in the cell or tissue component. This inhibitor/antagonist to elastase (which is beneficial to wound healing) can diffuse freely into the exudate and eventually pass to the wound bed, where it can act beneficially on it.

As an example of option c), a membrane with a suitable MWCO will allow significant amounts of solutes or disperse phase species to pass from the dialysate into the irrigant and/or wound exudate through the polymer film, sheet or membrane. This property may be used to perfuse materials beneficial to wound healing into the irrigant and/or exudate from a dialysate. In this less conventional type of infusion feed, a broad spectrum of species will usually pass into the exudate and/or irrigant fluid from the dialysate.

These include materials that are beneficial to wound healing and are expressed by the cell or tissue component.

Such materials include cytokines, enzymes, growth factors, and others having beneficial effects in causing chemotaxis.

These also include materials that are added elements beneficial to wound healing, such as
ionic species, such as bicarbonate;
vitamins, such as ascorbic acid (vitamin C) and vitamin E, and stable derivatives thereof, and mixtures thereof; to relieve oxidative stress on the wound bed;
pH buffering agents, such as potassium dihydrogen phosphate/disodium hydrogen phosphate,
local analgesics/anesthetics, such as lidocaine/lignocaine hydrochloride and xylocaine (adrenaline lidocaine) and/or anti-inflammatories, to reduce wound pain or inflammation or pain associated with the dressing nutrients to aid proliferation of wound cells, such as amino acids, sugars, low molecular weight tissue building blocks and trace elements; and other cell culture medium species; and
gases, such as air, nitrogen, oxygen and/or nitric oxide.

All such use of the present apparatus is, e.g. favourable to the wound healing process in chronic wounds, such as diabetic foot ulcers, and especially decubitus pressure ulcers.

Where it is desired to remove several different materials that are deleterious to wound healing, it may be advantageous to provide a system of modules in series, each of which removes a different material. This allows incompatible cell or tissue materials to be used on the same fluid and/or wound exudates.

Both the single-phase system and two-phase system may be in modular form that is relatively easily demountable from the apparatus of the invention. The system may suitably comprise one or more such modules.

Preferably any such system is a conventional automated, programmable system which can cleanse the wound irrigant and/or wound exudate with minimal supervision.

The means for fluid cleansing using cells or tissue may additionally, where appropriate, comprise one or more macroscopic and/or microscopic filters. These are to retain particulates, e.g. cell debris and micro-organisms, allowing proteins and nutrients to pass through.

The conduits through which respectively a) the irrigant and/or wound exudate passes from the wound dressing and b) the cleansed fluid, still containing materials from the wound that are beneficial in promoting wound healing, with added elements beneficial to wound healing to the exudate and irrigant (or modified irrigant), and/or modified through biochemical, enzymatic or physical means to contain elements beneficial to wound healing, is returned to the recirculation tube, and c) (in the case where the means is provided in the form of a two-phase system, such as an dialysis unit) through which the cleansing using cells or tissue fluid enters and exits the means preferably have means for, on module disconnection and withdrawal, i) switching off the flow and ii) providing an immediate fluid-tight seal or closure over the ends of the conduits and the cooperating tubes in the rest of the apparatus of the invention so exposed, to prevent continuing passage of irrigant and/or exudate and cleansed fluid, and cleansing using cells or tissue fluid.

The means for flow switching between supply and recirculation may take any form that enables the wound simultaneously to be a) put into communication with the fluid reservoir but b) closed to the fluid recirculation tube, and c) vice versa.

Thus, if there is only one inlet pipe that passes through and/or under the wound-facing face of the wound dressing, the fluid reservoir is connected by the fluid supply tube to the flow path via means for flow switching as desired the into a fluid recirculation tube or a fluid offtake tube.

In this case, the means for flow switching between supply and recirculation may be a regulator, such as a T-valve. This is connected in turn to two parts of a fluid recirculation tube or a fluid offtake tube and the fluid supply tube, such that the desired flow switching between supply and recirculation is achieved.

If there are two or more inlet pipes, these may be connected respectively to a fluid supply tube or fluid recirculation tube, respectively having a first regulator and a second regulator, such as a valve or other control device for admitting fluids into the wound.

The desired flow switching between supply and recirculation is achieved by respectively having the first regulator open when the second regulator is shut, and vice versa.

The means for bleeding the flowpath may be situated in any appropriate part of the apparatus that is in contact with the irrigant and/or wound exudate, but is usually within the offtake and/or recirculation tubes.

However, it is often as far downstream of and away from the reservoir and the fluid supply tube as possible, so that it may be used to prime the whole of the flowpath from the fluid reservoir via the fluid supply tube.

It may be a regulator, such as a valve or other control device, e.g. a T-valve that is turned to switch between bleed and recirculation, for bleeding fluids from the apparatus, e.g. to a waste reservoir, such as a collection bag. Alternatively, flow switching between supply and recirculation may not be desired, but rather concomitant bleeding and/or recirculation is desired.

The latter may occur when the volume of irrigant and/or wound exudate in recirculation is increased by continuing addition to it of a) wound exudate, and/or b) fluid passing from a cleansing fluid using cells or tissue through a selectively permeable integer, for example in a system such as a dialysis unit.

The means for bleeding the offtake and/or recirculation tubes may then be provided in the form of a regulator, such as a simple valve or other control device for admitting or blocking the passage of irrigant and/or exudate through a bleed line branching from the recirculation path.

In use, typically, the means for flow switching between supply and recirculation tubes is set to admit fluid into the wound from the fluid reservoir but to close the wound to the fluid recirculation tube.

Then, any means for bleeding the offtake and/or recirculation tubes are/is opened and the device for moving fluid through the wound and means for fluid cleansing using cells or tissue is started.

The capacity of the apparatus flow path and the flow rate of irrigant and/or wound exudate from the wound will largely determine whether it is appropriate to run the device to prime the apparatus throughout the whole length of the apparatus flow path, i.e. to displace any existing fluid reservoir (often air) from the fluid recirculation path, and for how long it should run.

Typically, there is a preponderance of irrigant from the fluid reservoir over wound exudate in recirculation, so that use of the device for moving fluid through the wound is appropriate for this purpose.

It is allowed to run until the apparatus is primed throughout the whole length of the apparatus flow path.

Then, typically the means for bleeding the offtake and/or recirculation tubes is closed, and the means for flow switching between supply and recirculation tubes is set to close the wound to the fluid reservoir but to admit fluid into the wound from the fluid recirculation tube.

If the means for fluid cleansing using cells or tissue is a two-phase system, the cleansing fluid is typically set in motion in contact with the surface of the selectively permeable integer, for example the polymer film, sheet or membrane. Of course, the cleansing fluid may less usually be static, and then this step is omitted.

As noted below in more detail, the volume of irrigant and/or wound exudate from the wound in recirculation may be increased by continuing addition to it of a) wound exudate, and/or b) fluid passing from a cleansing fluid through a selectively permeable integer, for example the polymer film, sheet or membrane of a two-phase system, such as an dialysis unit.

Additionally or alternatively, it may be desired to apply a negative pressure to the wound by means of a device for moving fluid through the wound and means for fluid cleansing using cells or tissue applied to the fluid in recirculation in the fluid recirculation tube downstream of and away from the wound dressing.

In such case, it may be desirable to provide a system in which concomitant bleeding and/or recirculation is possible, and to make the necessary adjustments to maintain the desired balance of fluid in recirculation by means of the means for bleeding the offtake and/or recirculation tubes.

The volume of irrigant and/or wound exudate from the wound in recirculation may be decreased by continuing loss from it of fluid passing from a cleansing fluid through a selectively permeable integer, for example in a system such as a dialysis unit.

Additionally or alternatively, it may be desired to apply a positive pressure to the wound by means of a device for moving fluid through the wound and means for fluid cleansing using cells or tissue applied to the fluid in recirculation in the fluid recirculation tube upstream of and towards the wound dressing.

The means for flow switching between supply and recirculation may be similarly provided in a form in which concomitant supply and/or recirculation is possible, and to make the necessary adjustments to maintain the desired balance of fluid in recirculation by means of the means for flow switching.

It will be appreciated that where a positive or negative pressure is to be applied to the wound, at least one hollow body in the recirculation flow path to and from the wound bed should have sufficient resilience against the pressure to allow any significant compression or decompression of the irrigant fluid to occur.

In all embodiments of the apparatus, the type and material of such bodies (which are defined by a film, sheet or membrane) that are described by way of example herein to be suitable for use in the present invention will be largely capable of this function.

Thus, examples of suitable materials for bodies defined by a film, sheet or membrane, such as inlet or offtake and/or recirculation tubes and structures such as bags, chambers and pouches, filled with irrigant fluid, e.g. the backing layer of the wound dressing are suitably elastically resilient thermoplastic materials that are potentially capable of this function when pressure is applied in this way.

The present invention in this aspect provides several advantages.

One is that application of a positive pressure to the wound under the backing layer may make it possible to flood the tissue underlying the wound with one or more physiologically active components.

This may be effected in therapeutically active amounts, to promote greater wound healing than by treatment with the fluid physiologically active component(s) alone.

Such physiologically active components of the exudate that are beneficial to wound healing may be e.g. be enzymes or other species and may be supplied from the dialysate of a dialytic means for fluid cleansing using cells or tissue.

It is believed that using the apparatus for aspirating, irrigating and/or cleansing wounds using cells or tissue of the present invention cyclically the effects may be further enhanced.

Circulating wound fluid aids in movement of biological signalling molecules involved in wound healing to locations in the wound bed that are favourable to the wound healing process and/or to cells that would otherwise not be exposed to them, e.g. in a highly exuding wound.

This is especially the case in those embodiments of the apparatus of this first aspect of the present invention for aspirating, irrigating and/or cleansing wounds using cells or tissue where there is an inlet or outlet manifold from which tubules radiate and run to the wound bed to end in openings that deliver and collect the fluid directly from the wound bed over an extended area.

In all embodiments of the apparatus of this first aspect of the present invention for aspirating, irrigating and/or cleansing wounds using cells or tissue, a particular advantage is the tendency of the wound dressing to conform to the shape of the bodily part to which it is applied.

The wound dressing comprises a backing layer with a wound-facing face which is capable of forming a relatively fluid-tight seal or closure over a wound and at least one inlet pipe for connection to a fluid supply tube or recirculation tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof;

polysiloxanes;

polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage.

(A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way.

Such means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound.

Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound. The device then applies a vacuum to the interior of the flange or lip, thus forming and maintaining a seal or closure acting at peripheral points around the wound against the positive pressure on the wound.

The wound dressing sealing periphery is preferably of a generally round shape, such as an ellipse, and in particular circular.

It may however be beneficial for the backing layer of the wound dressing as hereinbefore defined to extend from the generally round periphery of the wound dressing to define an arm that extends radially from the wound centre when the dressing is in use and covers the inlet and outlet pipes. This form of the dressing provides the opportunity for coupling and decoupling the irrigant supply remote from the dressing and the wound in use. An example is depicted in FIGS. 18 and 19.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of
a fluid recirculation tube and/or fluid supply tube (optionally or as necessary via means for forming a tube, pipe or hose, or nozzle, hole, opening, orifice, luer, slot or port for connection as a male member respectively to a mating end of
a fluid recirculation tube and/or fluid supply tube (optionally or as necessary via means for flow switching between supply and recirculation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components. The or each pipe will generally pass through, rather than under the backing layer.

In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid recirculation tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

The wound dressing may not comprise any integer under the backing layer in the wound in use.

However, this may not provide a system to distribute irrigant over a sufficient functional surface area to irrigate the wound at a practical rate. To be suitable for use, in particular in chronic wound dialysis, with relatively high concentrations of materials that are deleterious to wound healing, it may be advantageous to provide a system where wound irrigant and/or wound exudate may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the circulating fluid directly to the wound bed via the apertures. Similarly, there is an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred.

A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the circulating fluid directly to the wound bed or outlet pipe or collects the fluid directly from the wound respectively.

It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one which comprises one or more of the tubes, etc in a helix or spiral helix.

Other suitable layouts for shallower wounds include one which have blind-bore, perforated inlet pipe or outlet pipe manifolds that circulate fluid in the wound when the dressing is in use.

One or both of these may be such a form, the other may be, e.g. one or more straight blind-bore, perforated radial tubes, pipes or nozzles.

Another suitable layout is one in which
an inlet pipe and/or outlet pipe manifold that delivers the circulating fluid directly to the wound bed or collects the fluid directly from the wound respectively
via inlet and/or outlet tubes, pipes or tubules,
and the inlet manifold and/or outlet manifold is formed by slots in layers permanently attached to each other in a stack, and
the inlet and/or outlet tubes, pipes or tubules are formed by apertures through layers permanently attached to each other in a stack. (In FIG. 10a there is shown an exploded isometric view of such a stack, which is non-limiting.)

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings.

That is, up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape.

It is urged by its own resilience against the backing layer to apply gentle pressure on the wound bed.

The wound filler may be integral with the other components of the dressing, in particular the backing layer.

Alternatively, it may be permanently attached to them/it, with an adhesive film, for example, or by heat-sealing, e.g. to a flange or lip extending from the proximal face, so as not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other. The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic. Preferred materials for the present wound dressing include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials.

Examples also include aerosol foams, where the gaseous phase of the aerosol system is air or an inert gas, such as nitrogen or argon, more usually air, at a small positive pressure above atmospheric;

Examples also include solid particulates, such as plastics crumbs.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure, with apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the circulating fluid in the apparatus.

The hollow body or each of the hollow bodies then effectively forms an inlet pipe or outlet pipe manifold that delivers the circulating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the circulating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

The wound filler under the backing layer may effectively form an inlet pipe or outlet pipe manifold with a direct connection between the inlet pipe(s) and outlet pipe(s) at the point at which they pass through and/or under the wound-facing face and the wound bed is present.

Where it does not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler is an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that circulate fluid in the wound when the dressing is in use, that are described hereinbefore, may be used under a wound filler under the backing layer.

In brief, suitable layouts include ones where one or both manifolds are annular or toroidal (regular, e.g. elliptical or circular, or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid recirculation tube and the fluid supply tube, etc. may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should be suitably thick enough to withstand any positive or negative pressure on them, in particular if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted below with regard to pumps, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension.

They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for aspirating, irrigating and/or cleansing using wounds cells or tissue should be microbe-impermeable once the wound dressing is over the wound in use.

It is desirable that the wound dressing and the interior of the apparatus for aspirating, irrigating and/or cleansing wounds using cells or tissue of the present invention is sterile.

The fluid may be sterilised in the fluid reservoir and/or the rest of the system in which the fluid recirculates by ultraviolet, gamma or electron beam irradiation (except for the integer that contains the tissue or cell component, since this may adversely affect the viability and activity of the cells). This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in recirculation increased by continuing addition.

Examples of such materials include antibacterial agents (some of which are listed above), and antifungal agents.

Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate. may be added to adjust the pH, as may local analgesics/anaesthetics, such as lidocaine/lignocaine hydrochloride, xylocalne (adrenoline, lidocaine) and/or anti-inflammatories, to reduce wound pain or inflammation or pain associated with the dressing.

It is also desirable to provide a system in which physiologically active components of the exudate that are beneficial to wound healing are not removed before or after the application of fluid cleansing using cells or tissue.

This may occur, e.g. by the passive deposition of materials that are beneficial in promoting wound healing, such as proteins, e.g. growth factors. This may occur at any point in the flow path, e.g. in at least one inlet or outlet pipe.

The deposition of materials that are beneficial in promoting wound healing may be combated as follows:

a) extra materials may be added to the irrigant initially, and as desired the amount in recirculation increased by continuing addition, or b) a repellent coating may be used at any point or on any integer in the recirculation path in direct contact with the fluid, e.g. on the means for fluid cleansing using cells or tissue or any desired tube or pipe.

Examples of coating materials for surfaces over which the circulating fluid passes include anticoagulants, such as heparin, and high surface tension materials, such as PTFE, and polyamides, which are useful for growth factors, enzymes and other proteins and derivatives.

The apparatus of the invention for aspirating, irrigating and/or cleansing using cells or tissue wounds is provided with means for admitting fluids directly or indirectly to the wound under the wound dressing in the form of a fluid supply tube to a fluid reservoir.

The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers.

That is, up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds using cells or tissue and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system dialysis unit, of the dialysate that moves into the circulating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

The device for moving fluid through the wound and means for fluid cleansing using cells or tissue may be any appropriate for this purpose, and may act at any appropriate point for this purpose.

It may apply a positive or negative pressure to the wound, although its prime purpose is to move fluid (irrigant from the fluid reservoir and/or wound exudate through the length of the apparatus flow path, rather than to apply a positive or negative pressure to the wound.

If applied to the fluid in recirculation in the fluid recirculation tube upstream of and towards the wound dressing and/or the fluid in the fluid supply tube towards the wound dressing (optionally or as necessary via means for flow switching between supply and recirculation), it will usually apply positive pressure (i.e. above-atmospheric pressure) to the wound bed.

Often the means for fluid cleansing using cells or tissue is (most appropriately for its purpose) downstream of the wound dressing, and provides the highest resistance in the flow path.

This is especially the case where the means for fluid cleansing using cells or tissue is a single-phase system, e.g. with ultrafiltration through microapertures or micropores, thus enhancing applied positive pressure to the wound.

Where the device is applied to the fluid in recirculation in the fluid recirculation tube and/or the fluid in the fluid offtake tube downstream of and away from the wound dressing, it will usually apply negative pressure (i.e. below-atmospheric pressure or vacuum) to the wound bed.

Again, often the means for fluid cleansing using cells or tissue is (most appropriately for its purpose) downstream of the wound dressing, and provides the highest resistance in the flow path, thus enhancing applied negative pressure to the wound.

The following types of pump may be used as desired:

| reciprocating pumps, such as: | |
|---|---|
| shuttle pumps | with an oscillating shuttle mechanism to move fluids at rates from 2 to 50 ml per minute; |
| diaphragm pumps | where pulsations of one or two flexible diaphragms displace liquid while check valves control the direction of the fluid flow. |
| piston pumps | where pistons pump fluids through check valves, in particular for positive and/or negative pressure on the wound bed; |
| rotary pumps, such as: | |
| centrifugal pumps | |
| flexible impeller pumps | where elastomeric impeller traps fluid between impeller blades and a moulded housing that sweeps fluid through the pump housing. |
| progressing cavity pumps | with a cooperating screw rotor and stator, in particular for higher-viscosity and particulate-filled exudate; |
| rotary vane pumps | with rotating vaned disk attached to a drive shaft moving fluid without pulsation as it spins. The outlet can be restricted without damaging the pump. |
| peristaltic pumps | with peripheral rollers on rotor arms acting on a flexible fluid circulation tube to urge fluid current flow in the tube in the direction of the rotor. |
| vacuum pumps | with pressure regulators. |

The type and/or capacity of the device will be largely determined by
  a) the appropriate or desired fluid volume flow rate of irrigant and/or wound exudate from the wound, and
  b) whether it is appropriate or desired to apply a positive or negative pressure to the wound bed, and the level of such pressure to the wound bed
for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

In practice, even from a wound in a highly exuding state, such a rate of exudate flow is only of the order of up to 75 microliters/cm$^2$/hr (where cm$^2$ refers to the wound area), and the fluid can be highly mobile (owing to the proteases present). Exudate levels drop and consistency changes as the wound heals, e.g. to a level for the same wound that equates to 12.5-25 microliters/cm$^2$/hr.

Where materials deleterious to wound healing are removed by a two-phase system (see below.), such as a dialysis unit, fluid is also potentially lost to the system through the means for fluid cleansing using cells or tissue.

This may occur, e.g. through a dialysis polymer film, sheet or membrane which is also permeable to water, in addition to materials deleterious to wound healing.

The balance of fluid in recirculation may thus further decrease, but may be adjusted to minimise this undesired loss in a routine manner as described hereinbefore.

Hence, it will be seen that the circulating fluid from the wound will typically contain a preponderance of irrigant over wound exudate in recirculation from the fluid reservoir.

The type and/or capacity of the device will thus be largely determined in this respect by the appropriate or desired fluid volume flow rate of irrigant, rather than that of exudate, from the wound.

In practice, such a rate of flow of total irrigant and/or wound exudate will be of the order of 1 to 1000, e.g. 3 to 300, and less preferably 1 to 10 ml/cm$^2$/24 hour, where the cm$^2$ refers to the wound area.

The volume of irrigant and/or wound exudate in recirculation may vary over a wide range, but will typically be e.g. 1 to 8 l. (for example for large torso wounds), 200 to 1500 ml (for example for axillary and inguinal wounds), and 0.3 to 300 ml for limb wounds when the therapy is applied in this way.

In practice, suitable pressures are of the order of up to 25% atm such as up to 10% atm. positive or negative pressure on the wound bed, the apparatus being operated as a closed recirculating system.

The higher end of these ranges are potentially more suitable for hospital use, where relatively high % pressures and/or vacua may be used safely under professional supervision.

The lower end is potentially more suitable for home use, where relatively high % pressures and/or vacua cannot be used safely without professional supervision, or for field hospital use.

The device may be a peristaltic pump or diaphragm pump, e.g. preferably a small portable diaphragm or peristaltic pump. These are preferred types of pump, in order in particular to reduce or eliminate contact of internal surfaces and moving parts of the pump with (chronic) wound exudate, and for ease of cleaning.

It may suitably be one that applies positive pressure to the wound and/or the means for fluid cleansing using cells or tissue. A preferred pump when the applied pressure is positive is a peristaltic pump, e.g. a small, portable peristaltic pump, mounted upstream of the means for fluid cleansing using cells or tissue.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

The pump may suitably be one that applies negative pressure to the wound and/or the means for fluid cleansing using cells or tissue.

A preferred pump when the applied pressure is negative is a diaphragm pump, e.g. a small, portable diaphragm pump, mounted downstream of the dressing or the means for fluid cleansing using cells or tissue.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

The outlet from the dressing passes to the means for fluid cleansing using cells or tissue for removal of materials deleterious to wound healing from wound exudate, and in turn to the fluid recirculation tube(s).

The apparatus of the invention for aspirating, irrigating and/or cleansing using cells or tissue wounds is provided with means for bleeding the offtake and/or recirculation tubes, such as a regulator, such as a valve or other control device for bleeding fluids from the wound.

The device for moving fluid through the wound and means for fluid cleansing using cells or tissue is used to move irrigant to the wound dressing and apply the desired positive or negative pressure on the wound bed.

The desired balance of fluid in recirculation tube will typically be regulated by means of
a) the means for bleeding the offtake and/or recirculation tubes,
b) the means for flow switching between supply and recirculation, and/or
c) the means for moving fluid over the wound bed and through the means for fluid cleansing using cells or tissue,
as appropriate.

Thus, e.g. if
a) the apparatus for aspirating, irrigating and/or cleansing using cells or tissue wounds is a single-phase system, such as an ultrafiltration unit,
b) the wound is not in a highly exuding state and
c) it is not appropriate or desired to admit fluid into the wound from the fluid reservoir,
there is no or negligible change in the balance of fluid in recirculation.

Once it has been primed throughout, e.g. to the desired positive or negative pressure on the wound bed, the apparatus may be operated as a closed recirculating system.

The means for flow switching between supply and recirculation tubes is set to close the wound to the fluid reservoir via the fluid supply tube, and the means for bleeding the offtake and/or recirculation tubes are also closed.

If
a) the apparatus for aspirating, irrigating and/or cleansing using cells or tissue wounds is a single-phase system, such as an ultrafiltration unit,
b) the wound is in a highly exuding state and/or
c) it is appropriate or desired to admit fluid into the wound from the fluid reservoir,
there is a positive change in the balance of fluid in recirculation.

Once it has been primed throughout, e.g. to the desired positive or negative pressure on the wound bed, the apparatus cannot be operated as a closed recirculating system, without the pressure to the wound bed increasing, possibly undesirably.

The means for bleeding the offtake and/or recirculation tubes must be opened to some extent to relieve positive pressure on the wound bed. The bleed-off may be voided to waste, e.g. to a collection bag.

Materials that are beneficial in promoting wound healing may be lost to the site where they can be potentially of most benefit, i.e. the wound bed, when the therapy is applied in this way.

However, the balance of fluid in recirculation may be routinely adjusted to minimise this undesired loss.

The apparatus may have a two-phase system means for fluid cleansing using cells or tissue in the form of a dialysis container, e.g. a canister, cartridge or cassette, with one compartment through which the circulating fluid from the wound and the fluid reservoir passes and is separated by an integer that is permeable to materials in the circulating fluid in the apparatus, and a second compartment containing cells or tissue, through which passes a cleansing fluid.

The factors that determine the balance of fluid in recirculation in such an apparatus have been described hereinbefore in detail hereinbefore in connection with the operation of the apparatus. It is sufficient to note here that at some point after steady state recirculation established through the length of the apparatus flow path, it may be necessary that any bleed valve is opened, if overall the fluid level is increasing by transfer from the dialysate to an undesirable extent.

Other combinations, and the necessary adjustments to maintain the desired balance of fluid in recirculation tube by means of
a) the means for bleeding the offtake and/or recirculation tubes,
b) the means for flow switching between supply and recirculation, and/or
c) the means for moving fluid
will be apparent to the skilled person.

The outlet from the means for bleeding the offtake and/or recirculation tubes may be collected and monitored and used to diagnose the status of the wound and/or its exudate.

The waste reservoir may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the waste reservoir will be largely determined by its function.

To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a second aspect of the present invention there is provided a conformable wound dressing, characterised in that it comprises a backing layer with a wound-facing face which is capable of forming a relatively fluid-tight seal or closure over a wound and has at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound.

The dressing is advantageously provided for use in a bacteria-proof pouch.

In some embodiments of the present invention there may be a wound contact layer. The wound contact layer may be made from any suitable material known in the art (e.g. gauze or foam) which will allow nutrients to reach the wound bed. Having a wound contact layer may prevent overgrowth of the granulation material.

In some embodiments of the present invention, a significant advantage, in particular in chronic wounds, is that in use granulation tissue is encouraged to grow onto and/or into the wound contact layer that lies between the wound film dressing and the wound bed.

The effect may be further enhanced by the circulation over the wound bed of irrigant from the fluid reservoir which contains nutrients for wound cells to aid proliferation, and other molecules that are beneficially involved in wound healing and/or that are favourable to the wound healing process.

A further particular advantage is that it is unnecessary to remove this granulation tissue in-growth on dressing change, as the wound contact layer may be left between the wound film dressing and the wound bed biodegrade. This minimises trauma and any need for debridement.

A particular advantage of this wound contact layer is its use with pressure sores: the device can be placed in the depths of the wound and the patient can lie upon it without either affecting the utility of the device or further damaging the wound. This becomes critical if the patient cannot be moved from this posture for other medical reasons.

The wound contact layer is placed over substantially the expanse of the wound, and its size and configuration can be adjusted to fit the individual wound. It can be formed from a variety of apertured, semi-rigid materials.

By 'apertured' herein is meant materials that are porous, apertured, holed, open-mesh, slit, incised and/or cut.

The material must be sufficiently apertured to allow for invasion by all manner of cells involved in the process of tissue repair and wound healing, and/or for the inward growth of blood vessels, and sufficiently rigid to prevent overgrowth and collapse under suction.

Suitable biomaterials for a biodegradable wound contact layer include poly(hydroxy acids) and esters thereof, such as poly(glycolic acid), poly(L-lactic acid), poly(D-lactic acid) and esters thereof, and copolymers and blends of the aforementioned.

Suitable biomaterials also include poly(acid anhydrides), such as poly(terephthalic acid), poly(adipic acid) and copolymers and blends of the aforementioned.

Additionally, biologically sourced biodegradable polymeric materials may be used, such as substantially protein based polymers, for example collagens, fibronectins, or fibrins, either as whole molecules or those subjected to proteolytic or chemical treatments, in either degraded or native conformations, or modified protein based polymers produced by nucleic acids recombinant techniques, for example, collagens, fibronectins, or fibrins, or fragments thereof, produced through recombinant DNA techniques; or blends thereof.

Further acceptable wound contact layers will be combinations of protein based scaffolds and carbohydrate based polymers such as glycosoaminoglycans, chitosans, cellulose or alginate molecules.

Suitable materials also include human or animal derived tissues processed in means to make them acceptable in placement into the wound such as skin, alimentary tract or connective tissues.

The wound contact layer/material may be formed in a variety of apertured, semi-rigid forms.

These forms may be essentially two-dimensional, such as sheets, layers, films, flexible panels, meshes, nets, webs or lattices. They may be placed in the wound as dry, hydrated or gel based formulations.

One embodiment of apertured or holed scaffold comprises a section of honeycombed polymer sheet cut to the shape of the wound.

Where the wound contact layer is in an essentially two-dimensional apertured, semi-rigid form, such as a sheet, layer, film, flexible panel, mesh, net, web or lattice, it may be designed in a configuration that is able to conform well to the wound bed on insertion into the wound.

This conforming to shape is then a particular advantage in those embodiments where the wound dressing is used on deeper wounds, especially where a wound filler is used to urge the wound dressing towards the wound contact layer and wound bed, as described hereinafter in connection with the wound dressing.

By way of example, such a wound contact layer may be in the form of a deeply indented circular disc much like a multiple Maltese cross or a stylised rose. This form is able to conform well to the wound bed on insertion into the wound, especially a deeper wound, by the arms closing in and possibly overlapping.

The form of the wound contact layer may also be three-dimensional, such as sheets, layers, films, flexible panels, meshes, nets, webs and lattices, folded, creased, pleated, tucked, crinkled, crumpled, screwed up or twisted into a three-dimensional form.

Alternatively, these forms may be inherently three-dimensional, such as multilayers of films, flexible panels, meshes, nets, webs and lattices, or three-dimensional meshes, nets, webs and lattices, and favourably foams. They may be placed in the wound as dry, hydrated or gel based formulations.

Examples of suitable forms of such wound dressings are as described by way of example hereinbefore.

It is an object of the present invention
e) to obviate at least some of the disadvantages of known aspiration and/or irrigation therapies, and
f) to provide a system of therapy which
  i) can remove materials deleterious to wound healing from wound exudate, whilst retaining and/or adding materials that are beneficial in promoting wound healing in contact with the wound bed, and/or
  ii) which allows fluids containing active amounts of materials that are beneficial in promoting wound healing to pass into and/or through the wound in contact with the wound bed.

Embodiments of the present invention may also include:
a suction head having a first face;
a second face opposite said first face, wherein said second face is comprised of a plurality of projections, said projections defining a plurality of channels for facilitating flow of fluids to an opening in said second face and through said first face, wherein said opening is adapted for connection to a suction tube; and
a surgical drape having an aperture coincident said opening, said surgical drape extending over a region, and overlapping beyond the perimeter of said first face, and wherein said surgical drape comprises a flexible adhesive coated film adhered to said region of said first face and a release-coated backing extending over said second face and adhered to the overlapping portion of said surgical drape.

For distributing fluid across a wound surface, the present invention may also include:
a suction head having a first face;
a second face opposite said first face;
a plurality of projections coincident from said second face, wherein said projections form a contact surface with the wound surface, and wherein a plurality of channels for facilitating flow of fluids are defined between said projections, said channels remaining out of contact with the wound surface; and
an aperture in fluid communication with said channels formed by said projections and formed through said first face and second face.

Embodiments of the present invention may also comprise:
a method of using a therapeutic apparatus for stimulating the healing of wounds in mammals comprising the steps of:
inserting a porous pad into or on said wound such that said porous pad is in contact with said wound, wherein said porous pad has at least a partial outer surface and an inner body, said outer surface being adapted for contact with surface of said wound with small first pores no larger than about 100 microns in diameter to enhance biocompatibility;
securing said porous paid within said wound with the dressing cover to maintain a negative pressure at the site of said wound;
generating a negative pressure at said wound through said porous pad; and
collecting fluids from said wound through said porous pad.

Thus, in a third aspect of the present invention there is provided a method of treating wounds to promote wound healing using the apparatus for aspirating, irrigating and/or cleansing using cells or tissue wounds of the present invention.

The present invention will now be described by way of example only with reference to the accompanying drawings in which:

FIG. 1 is a schematic view of an apparatus for aspirating, irrigating and/or cleansing using cells or tissue a wound according to the first aspect of the present invention.

It has a single-phase system means for fluid cleansing using cells or tissue in the form of a container, e.g. a canister, cartridge or cassette, with a chamber or compartment that contains a cell or tissue component, through which the wound exudate or a mixture with irrigant passes.

FIG. 2 is a schematic view of an apparatus for aspirating, irrigating and/or cleansing using cells or tissue a wound according to the first aspect of the present invention.

It has a two-phase system means for fluid cleansing using cells or tissue in the form of a dialysis container, e.g. a canister, cartridge or cassette, with one compartment through which the circulating fluid from the wound and the fluid reservoir passes and is separated by an integer that is permeable to materials in the circulating fluid in the apparatus from a second compartment containing cells or tissue, through which passes a cleansing fluid.

FIGS. 3 to 7 are cross-sectional views of conformable wound dressings, of the second aspect of the present invention for aspirating and/or irrigating wounds.

In these, FIGS. 3a to 6a are cross-sectional plan views of the wound dressings, and FIGS. 3b to 6b are cross-sectional side views of the wound dressings.

FIGS. 8 to 10 are various views of inlet and outlet manifold layouts for the wound dressings of the second aspect of the present invention for respectively delivering fluid to, and collecting fluid from, the wound.

FIG. 11 is a schematic view of an apparatus for aspirating, irrigating and/or cleansing using cells or tissue a wound according to the first aspect of the present invention.

It has a single-phase system means for fluid cleansing using cells or tissue in the form of a container, e.g. a canister, cartridge or cassette, with a chamber or compartment that contains a cell or tissue component, through which the wound exudate or a mixture with irrigant passes.

Figure 12:
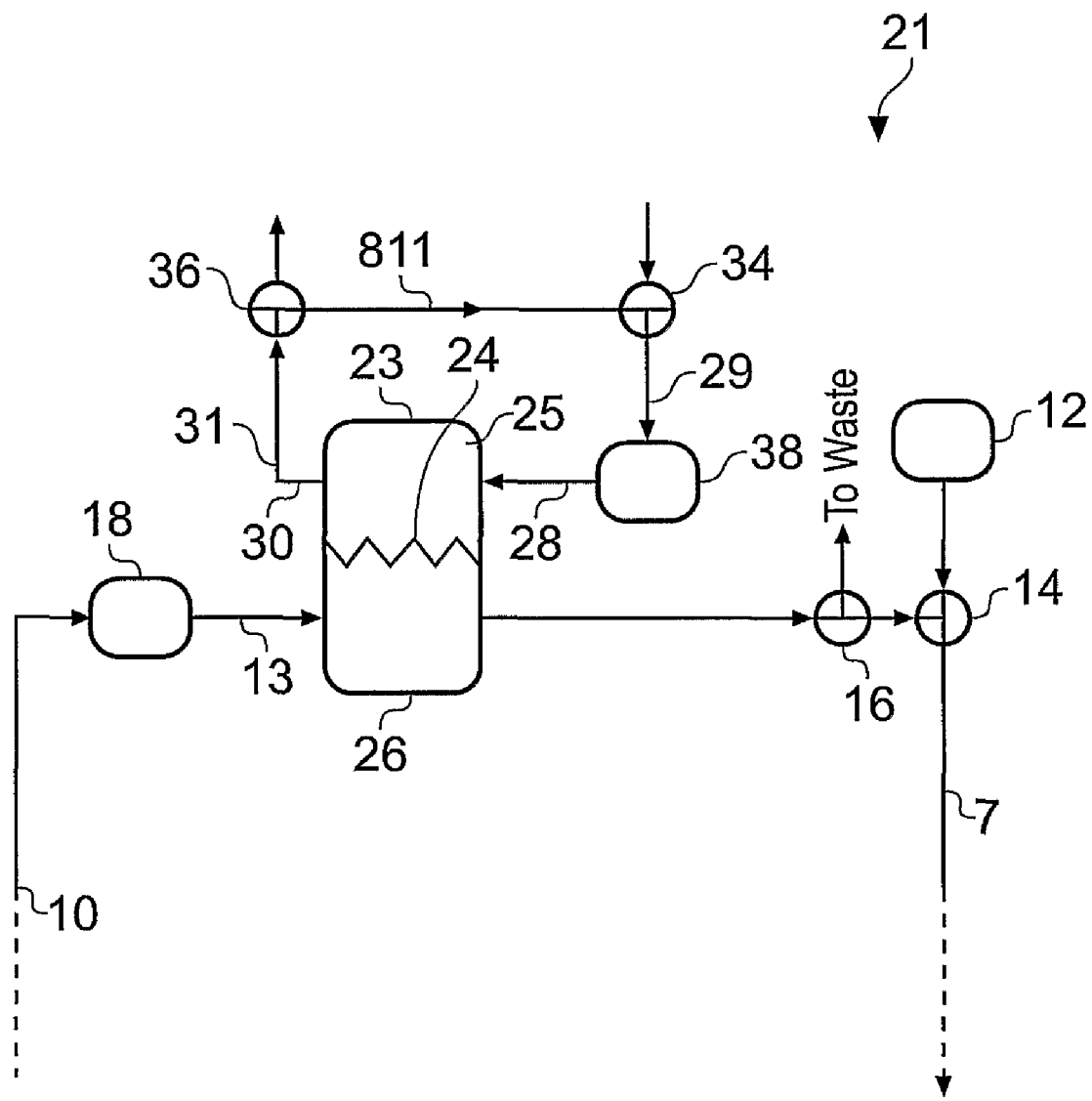

FIG. 12 is a schematic view of an apparatus for aspirating, irrigating and/or cleansing using cells or tissue a wound according to the first aspect of the present invention.

It has a two-phase system means for fluid cleansing using cells or tissue in the form of a dialysis container, e.g. a canister, cartridge or cassette, with one compartment through which the circulating fluid from the wound and the fluid reservoir passes and is separated by an integer that is permeable to materials in the circulating fluid in the apparatus from a second compartment containing cells or tissue, through which passes a cleansing fluid.

FIGS. 13 to 26 are cross-sectional views of conformable wound dressings, of the second aspect of the present invention for aspirating and/or irrigating wounds.

FIG. 27 is a schematic view of another apparatus for aspirating, irrigating and/or cleansing using cells or tissue a wound according to the first aspect of the present invention.

Figure 28:
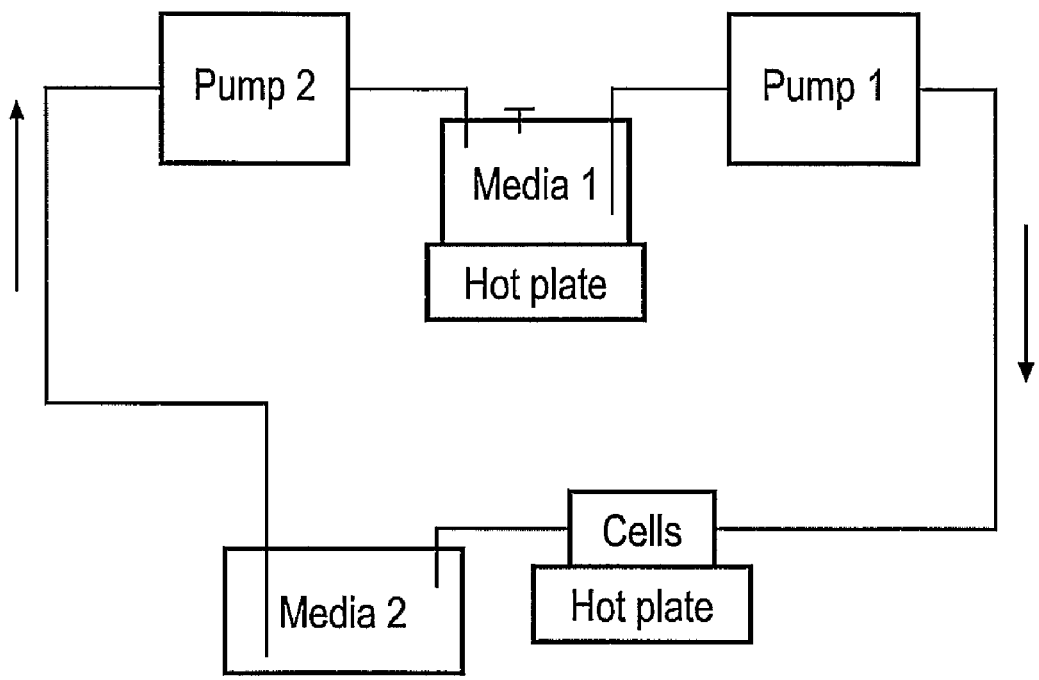

FIG. 28 shows a schematic representation exudialysis flow system according to the present invention.

Figure 29:
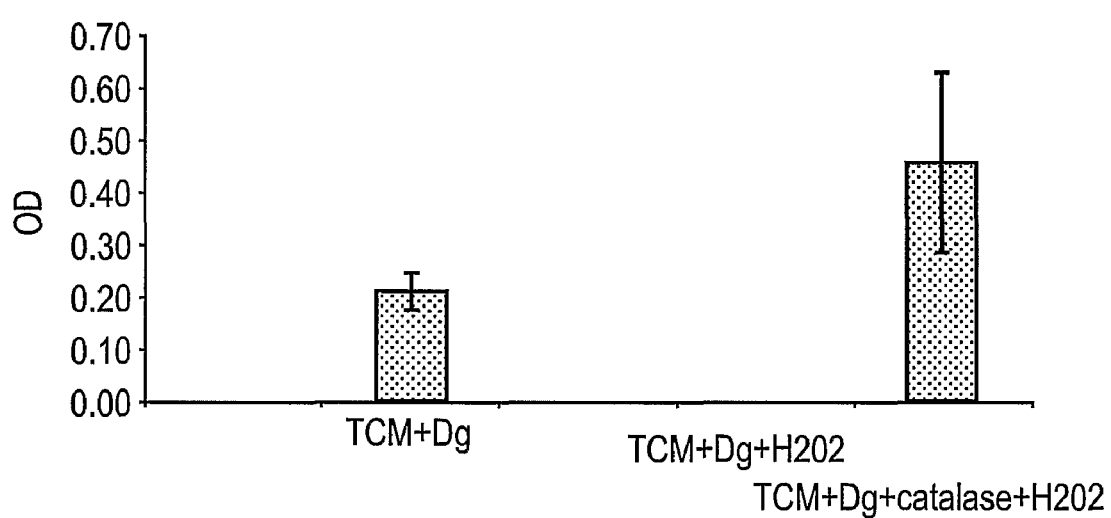

FIG. 29 shows average WST activity of fibroblasts on
a) control (TCM+Dg) of media and cells
b) media, cell and Hydrogen peroxide (TCM+Dg+$H_2O_2$); and
c) media, cells, Hydrogen peroxide and exudialysis (TCM+Dg+catalase+$H_2O_2$)

It has a single-phase system means for fluid cleansing using cells or tissue, in the form of a container, e.g. a canister, cartridge or cassette, with a chamber or compartment that contains a cell or tissue component, through which the wound exudate or a mixture with irrigant passes.

Figure 1:
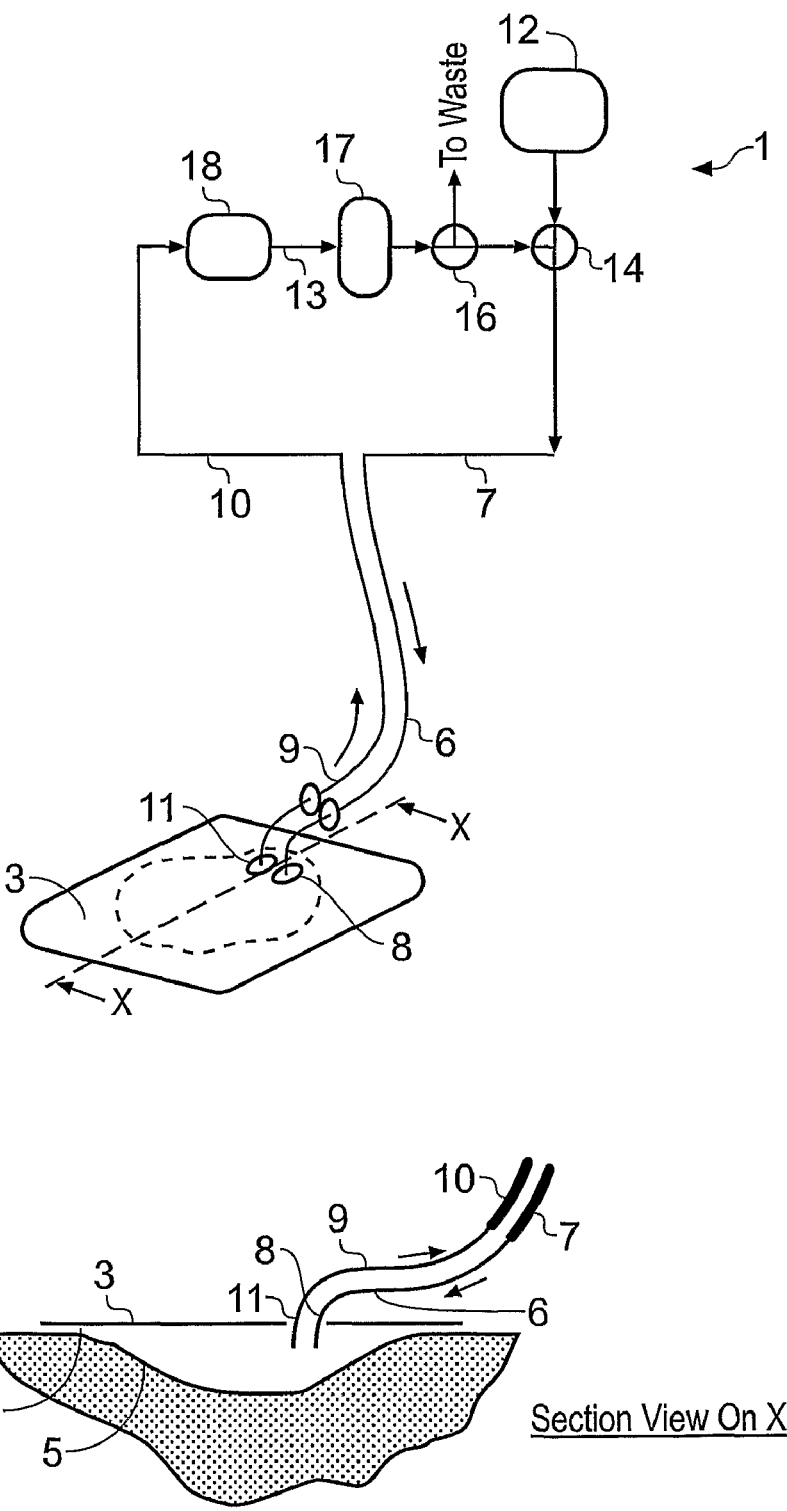

Referring to FIG. 1, the apparatus (1) for aspirating, irrigating and/or cleansing using cells or tissue wounds comprises
a conformable wound dressing (2), having
a backing layer (3) which is capable of forming a relatively fluid-tight seal or closure (4) over a wound (5) and
one inlet pipe (6) for connection to a fluid supply tube (7), which passes through the wound-facing face of the backing layer (3) at (8), and
one outlet pipe (9) for connection to a fluid offtake tube (10), which passes through the wound-facing face of the backing layer (3) at (11),
the points (8), (11) at which the inlet pipe and the outlet pipe passes through and/or under the backing layer (3) wound-facing face forming a relatively fluid-tight seal or closure over the wound,
the inlet pipe being connected via means for flow switching between supply and recirculation, here a T-valve (14), by the fluid supply tube (7) to a fluid reservoir (12) and to a fluid recirculation tube (13) having a means for bleeding the tube, here a bleed T-valve (16) to waste, e.g. to a collection bag (not shown),
the outlet pipe (9) being connected to a fluid offtake tube (10), connected in turn to
means for fluid cleansing using cells or tissue (17), here in the form of a container, e.g. a canister, cartridge or cassette, with a chamber or compartment that contains a cell or tissue component, through which the wound exudate or a mixture with irrigant passes, connected to the inlet pipe (6) via the fluid recirculation tube (13) and T-valve (14), and
a device for moving fluid through the wound and means for fluid cleansing using cells or tissue (17), here a peristaltic pump (18), e.g. preferably a small portable peristaltic pump, acting on the fluid circulation tube (13) with the peripheral rollers on its rotor (not shown) to apply a low negative pressure on the wound.

The means (17) is a single-phase system. In this the circulating fluid from the wound and the fluid reservoir passes through a self-contained system in which materials deleterious to wound healing are removed and the cleansed fluid, still containing materials from the wound that are beneficial in promoting wound healing,
with added elements beneficial to wound healing to the exudate and irrigant (or modified irrigant),
modified through biochemical, enzymatic or physical means to contain elements beneficial to wound healing, is returned via the recirculation tube to the wound bed.

(In a variant of this apparatus, there are two inlet pipes (6), which are connected respectively to a fluid supply tube (7) and fluid recirculation tube (13), respectively, having a first valve for admitting fluid into the wound from the fluid reservoir (12) and a second valve for admitting fluid into the wound from the recirculation tube.

Usually in use of the apparatus, when the first valve is open, the 10 second valve (20) is shut, and vice versa.)

In use of the apparatus (1), the valve (16) is opened to a collection bag (not shown), and the T-valve (14) is turned to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve for admitting fluid into the wound from the fluid reservoir (12) is opened and the second valve is shut, and vice versa.)

The pump (18) is started to nip the fluid recirculation tube (13) with the peripheral rollers on its rotor (not shown) to apply a low positive pressure on the wound. It is allowed to run until the apparatus is primed throughout the whole length of the apparatus flow path and excess fluid is voided to waste via the bleed T-valve (16) into the collection bag (not shown).

The T-valve (14) is then turned to switch from supply and recirculation, i.e. is set to close the wound to the fluid reservoir (12) but to admit fluid into the wound from the fluid recirculation tube (13), and the bleed T-valve (16) is simultaneously closed.

(In the variant of this apparatus, where there are two inlet pipes (6), which are connected respectively to a fluid supply tube (7) and fluid recirculation tube (13), the first valve is closed and a recirculating system set up by opening the second valve for admitting fluid into the wound from the recirculation tube (13).

The circulating fluid from the wound and the fluid reservoir (12) passes through the cleansing means (17). Materials deleterious to wound healing are removed and the cleansed fluid, still containing materials from the wound that are beneficial in promoting wound healing,
with added elements beneficial to wound healing to the exudate and irrigant (or modified irrigant), and/or
modified through biochemical, enzymatic or physical means to contain elements beneficial to wound healing, is returned via the recirculation tube (13) to the wound bed.

The recirculation of fluid may be continued as long as desired.

Switching between supply and recirculation is then reversed, by turning the T-valve (14) to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve for admitting fluid into the wound from the fluid reservoir (12) is opened and the second valve is shut, and vice versa.)

The bleed valve (16) is simultaneously opened, so that fresh fluid flushes the recirculating system.

The running of the pump (18) may be continued until the apparatus is flushed, when it and the fluid recirculation is stopped.

If, e.g. the wound is in a highly exuding state, there is a positive change in the balance of fluid in recirculation.

It may be necessary to bleed fluid from recirculation, by opening the bleed T-valve (16) to bleed fluid from the recirculation tube (13).

Figure 2:
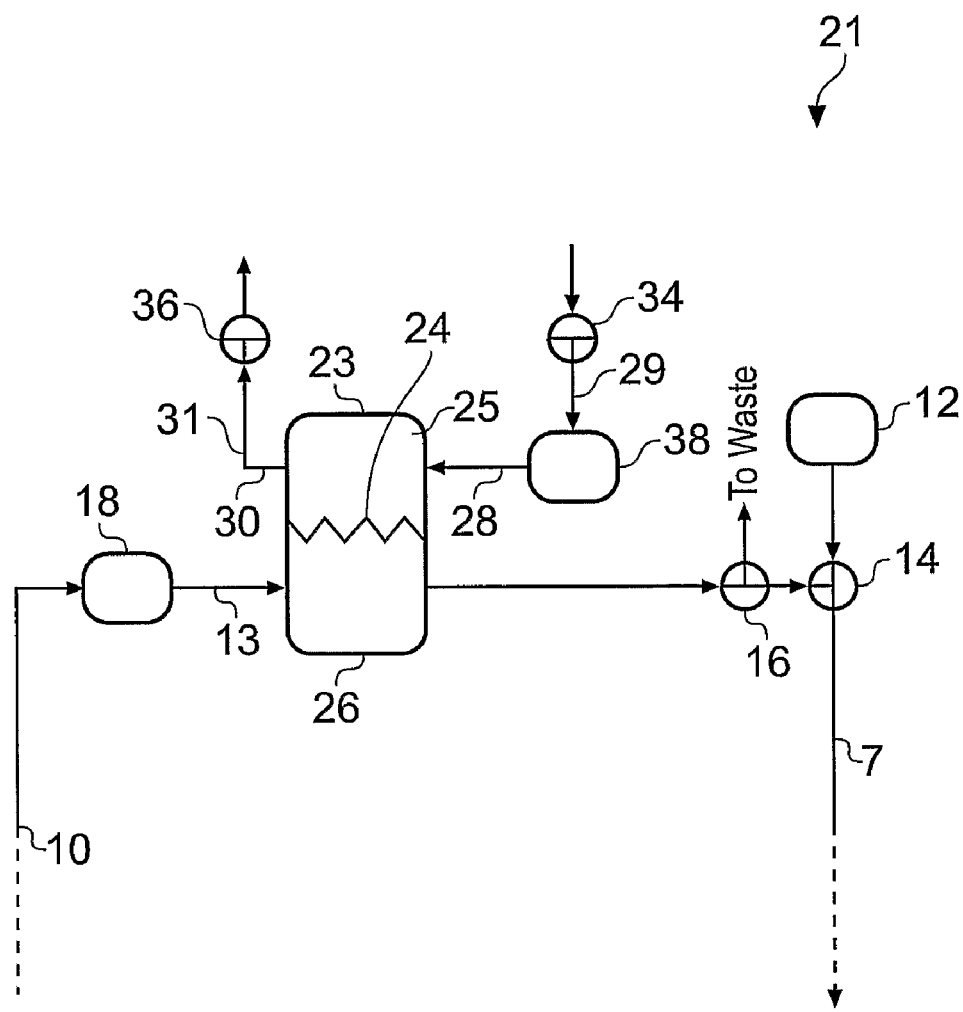

Referring to FIG. 2, the apparatus (21) is a variant of that of FIG. 1, with identical, and identically numbered, components, except for the means for fluid cleansing using cells or tissue, which is in the form of a two-phase system (23).

The unit (23) thus has an internal polymer film, sheet or membrane (24), selectively permeable to materials deleterious to wound healing, which divides it into
a) a first chamber (26), through which passes the circulating fluid from the wound and the fluid reservoir (12), and from which deleterious materials are removed, and
b) a first chamber (25), containing cells or tissue, through which passes a cleansing fluid across one surface of the polymer film, sheet or membrane The unit (23) thus has a dialysate inlet pipe (28) connecting to a dialysate supply tube (29) which passes to a peristaltic pump (38), e.g. preferably a small portable peristaltic pump, acting on the dialysate supply tube (29) with the peripheral rollers on its rotor (not shown) to supply cleansing using cells or tissue fluid across the surface of the polymer film, sheet or membrane (28) in the first chamber (25) from a dialysate reservoir (not shown) via a valve (34).

The dialysis unit (23) also has a dialysate outlet pipe (30) connecting to a dialysate outlet tube (31) which passes to waste via a second bleed T-valve (36) into, e.g. a collection bag (not shown).

Operation of this apparatus is similar to that of FIG. 1, except for the dialysis unit (23), in that at some point after the irrigation system is primed and steady state recirculation established through the length of the apparatus flow path, the valve (34) and second bleed valve (36) are opened.

The pump (38) is started to nip fluid dialysate tube (29) with the peripheral rollers on its rotor (not shown) to pump cleansing using cells or tissue fluid to the first chamber from a dialysate reservoir (not shown) and out to waste via the bleed valve (36) into the collection bag (not shown).

The dialysis unit (23) is a module (or scrubbing cartridge) with a substrate that changes colour to indicate the presence of detrimental factors in the cleansed fluid, and that the scrubbing cartridge is exhausted and should be renewed.

Referring to FIGS. 3 to 6, each dressing (41) is in the form of a conformable body defined by a microbe-impermeable film backing layer (42) with a uniform thickness of 25 micron, with a wound-facing face (43) which is capable of forming a relatively fluid-tight seal or closure over a wound.

In use, the backing layer (42) extends on a wound over the skin around the wound.

On the proximal face of the backing layer (43) on the overlap (44), it bears an adhesive film (45), to attach it to the skin sufficiently to hold the wound dressing in place in a fluid-tight seal around the periphery of the wound-facing face (43) of the wound dressing.

There is one inlet pipe (46) for connection to a fluid supply tube (not shown), which passes through and/or under the wound-facing face (43), and one outlet pipe (47) for connection to a fluid offtake tube (not shown), which passes through and/or under the wound-facing face (43) of the backing layer.

Figure 3A:
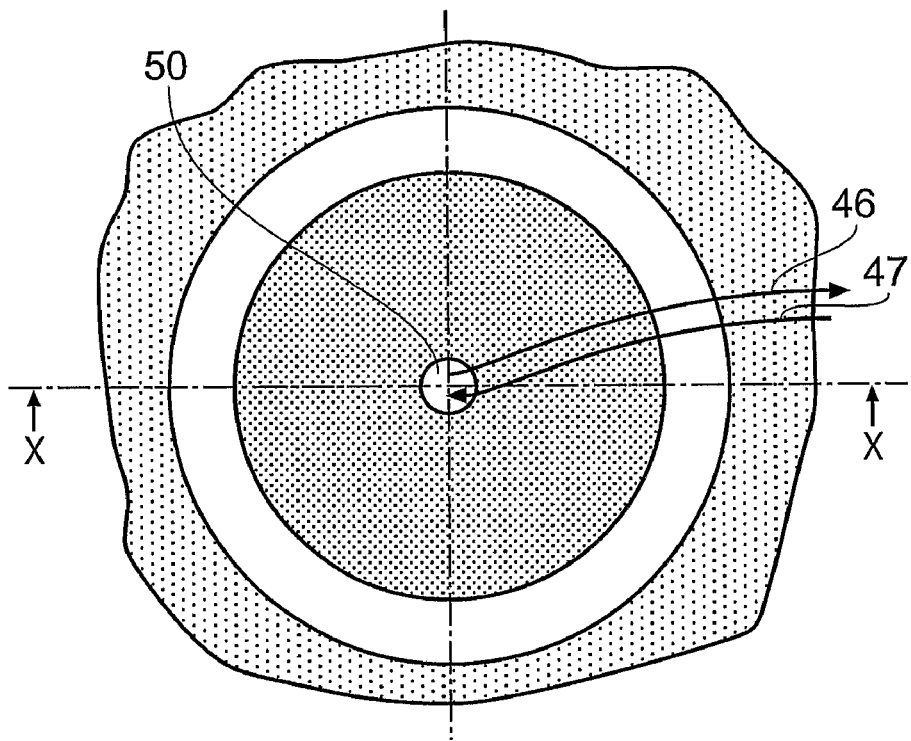
Figure 3B:
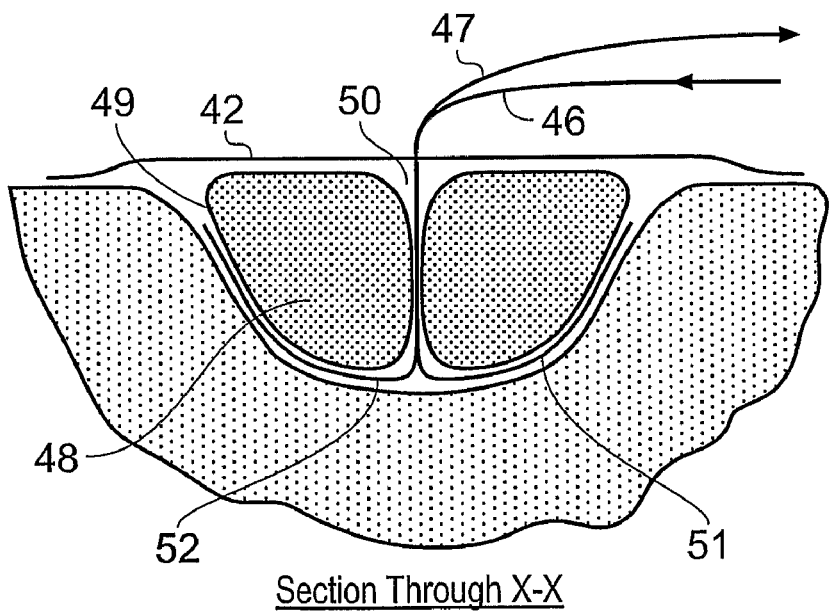

Referring to FIGS. 3a and 3b, one form of the dressing is provided with a wound filler (48) under a circular backing layer (42).

This comprises a generally frustroconical, toroidal conformable hollow body, defined by a membrane (49) which is filled with a fluid, here air or nitrogen, that urges it to the wound shape.

The filler (48) may be permanently attached to the backing layer with an adhesive film (not shown) or by heat-sealing.

The inlet pipe (46) and outlet pipe (47) are mounted centrally in the backing layer (42) above the central tunnel (50) of the toroidal hollow body (48) and each passes through the backing layer (42), and each extends in pipes (51) and (52) respectively through the tunnel (50) of the toroidal hollow body (48) and then radially in diametrically opposite directions under the body (48).

This form of the dressing is a more suitable layout for deeper wounds.

Figure 4A:
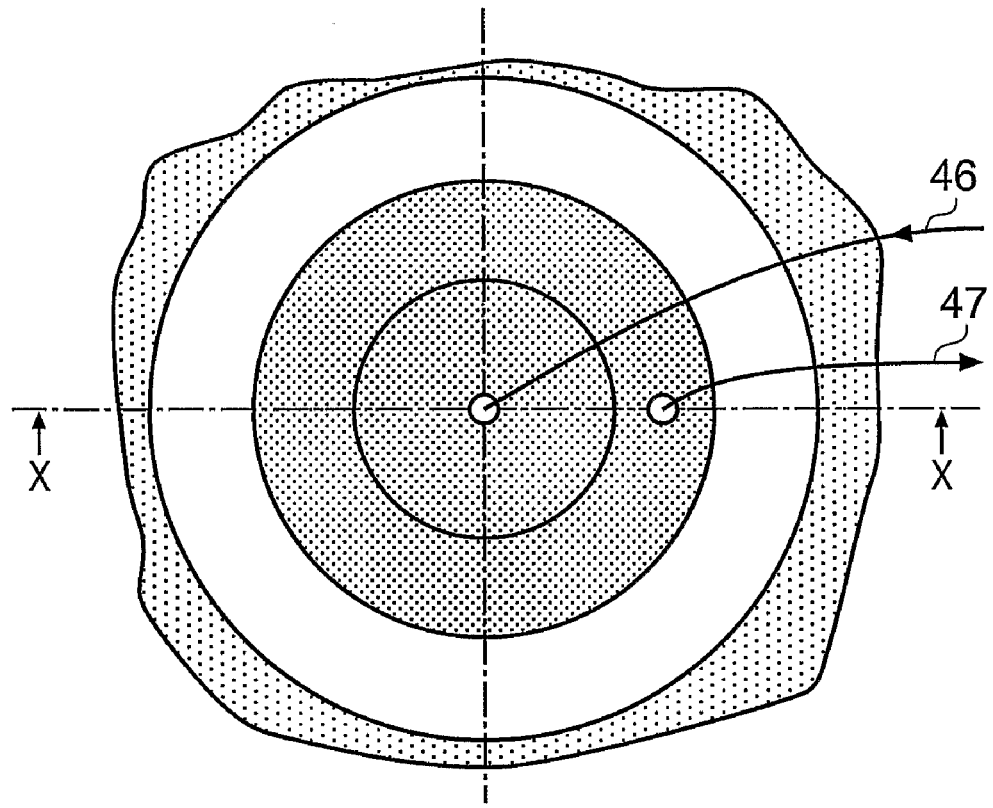
Figure 4B:
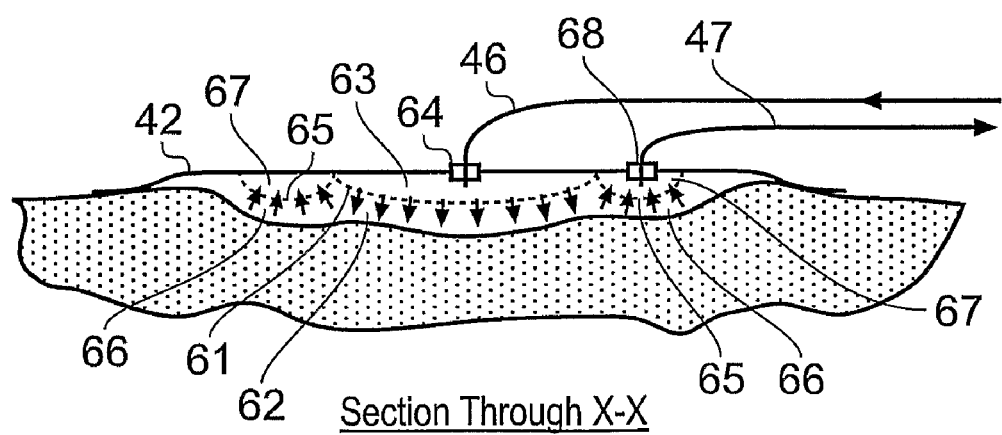

Referring to FIGS. 4a and 4b, a more suitable form for shallower wounds is shown. This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the circulating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Figure 5A:
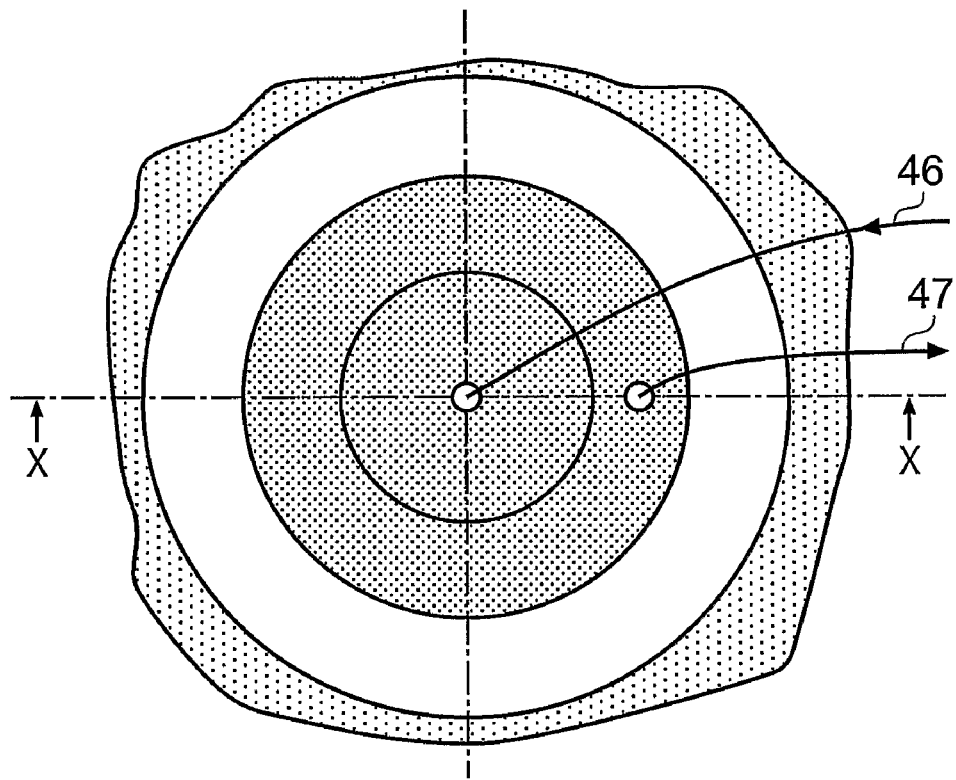
Figure 5B:
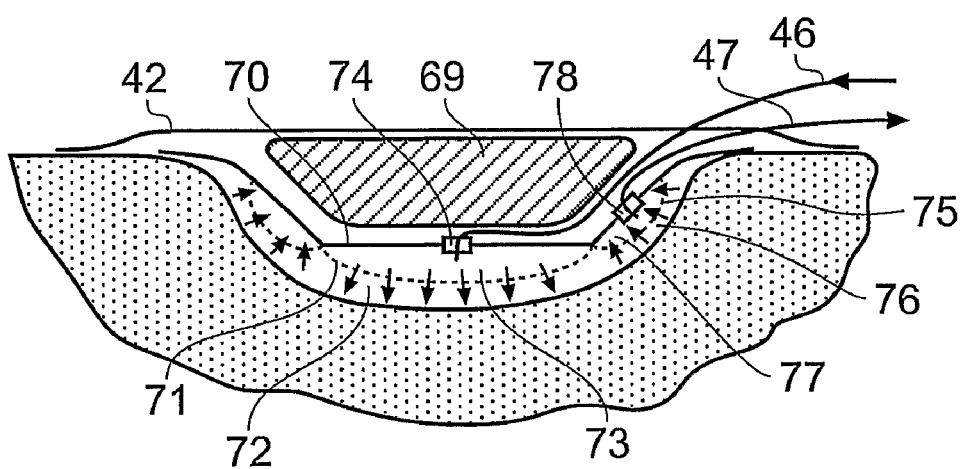

Referring to FIGS. 5a and 5b, a variant of the dressing of FIGS. 4a and 4b that is a more suitable form for deeper wounds is shown.

This comprises a circular backing layer (42) and a filler (69), in the form of an inverted frustroconical, solid integer, here a resilient elastomeric foam, formed of a thermoplastic, or preferably a cross-linked plastics foam.

It may be permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the circulating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (47) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42).

Figure 6A:
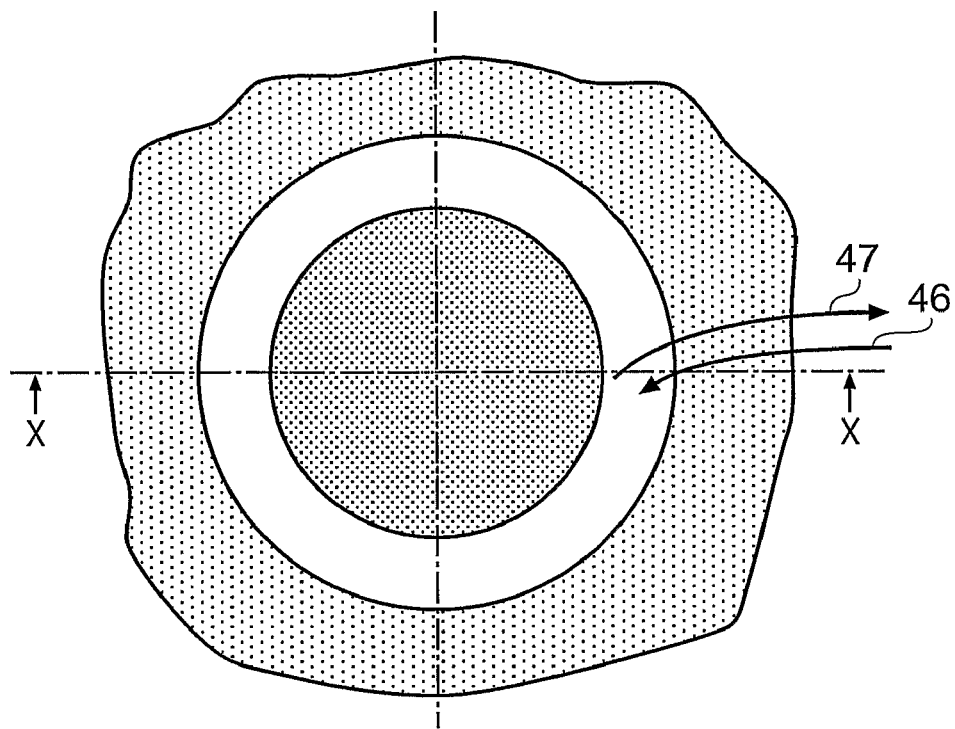
Figure 6B:
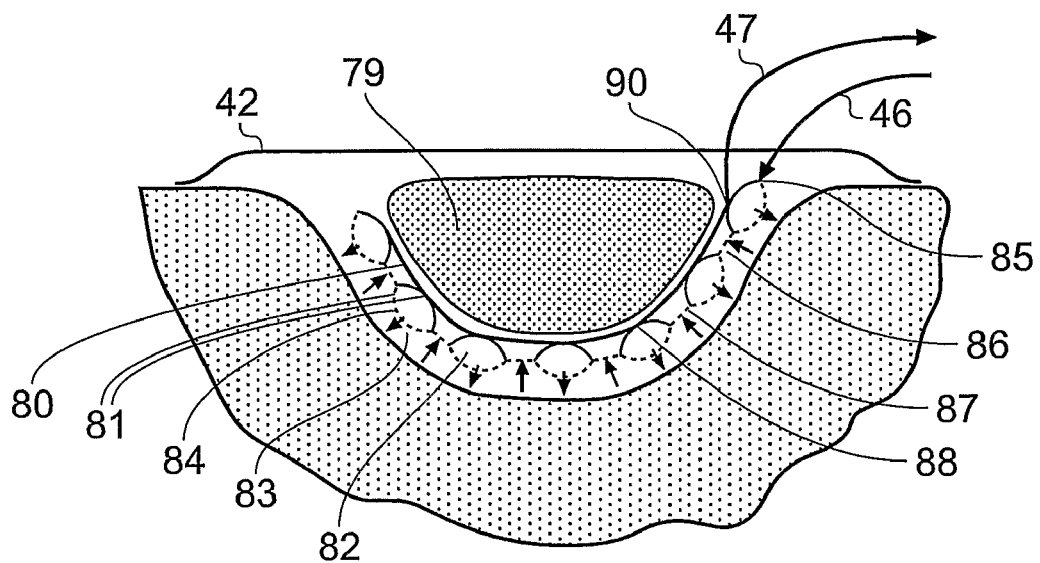

Referring to FIGS. 6a and 6b, a dressing that is a more suitable form for deeper wounds is shown.

This comprises a circular backing layer (42) and a filler (79), in the form of an inverted generally hemispherical integer, here a resilient elastomeric foam or a hollow body filled with a fluid, here a gel that urges it to the wound shape, and permanently attached to the backing layer with an adhesive film (not shown) or by heat-sealing.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with perforations (83) along its length on the outer surface (84) of
the dish formed by the membrane (81) and an opening (85) at the outer end of its spiral helix, through which the channel (82) communicates with the inlet pipe (46), and thus effectively forms an inlet pipe manifold that delivers the circulating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Figure 7A:
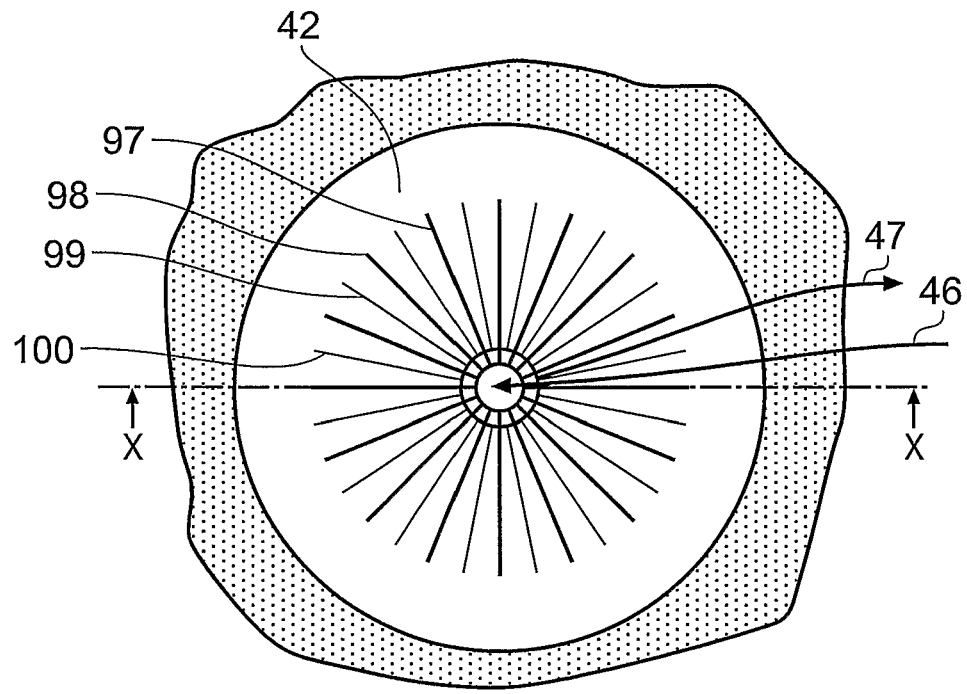
Figure 7B:
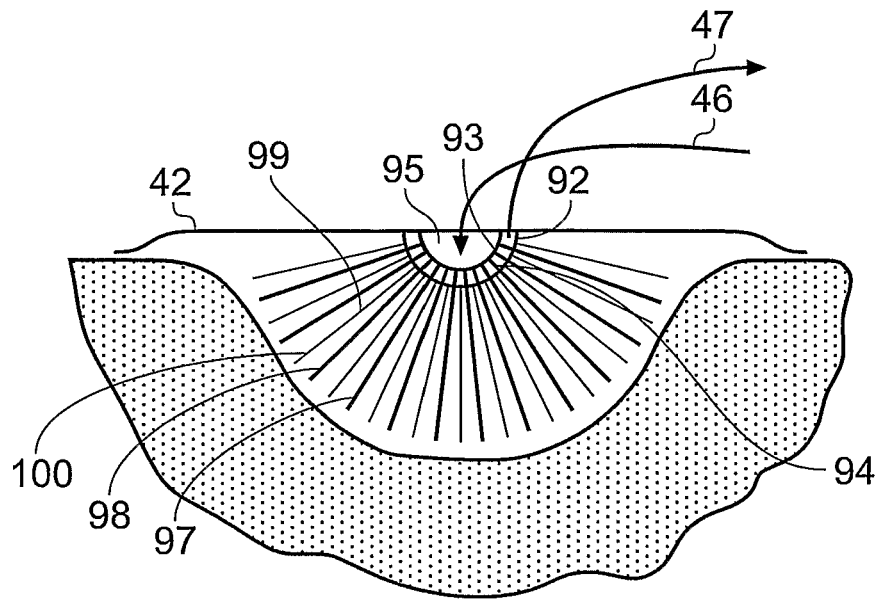

Referring to FIGS. 7*a* and 7*b*, one form of the dressing is provided with a circular backing layer (42). A first (larger) inverted hemispherical membrane (92) is permanently attached centrally to the layer (42) by heat-sealing to form a hemispherical chamber (94) with the layer (42). A second (smaller) concentric hemispherical membrane (93) within the first is permanently attached to the layer (42) by heat-sealing to form a hemispherical pouch (95).

The pouch (95) communicates with the inlet pipe (46) and is thus effectively an inlet manifold, from which pipes (97) radiate hemispherically and run to the wound bed to end in apertures (98). The pipes (97) deliver the circulating fluid directly to the wound bed via the apertures (98).

The chamber (94) communicates with the outlet pipe (47) and is thus effectively an outlet manifold from which tubules (99) radiate hemispherically and run to the wound bed to end in openings (100). The tubules (99) collect the fluid directly from the wound via the openings (100).

Referring to FIGS. 8*a* to 8*d*, one form of the dressing is provided with a square backing layer (42) and
first tube (101) extending from the inlet pipe (46), and
second tube (102) extending from the outlet pipe (47)
at the points at which they pass through the backing layer, to run over the wound bed.

These pipes (101), (102) have a blind bore with orifices (103), (104) along the pipes (101), (102). These pipes (101), (102) respectively form an inlet pipe or outlet pipe manifold that delivers the circulating fluid directly to the wound bed or collects the fluid directly from the wound respectively via the orifices.

Figure 8A:
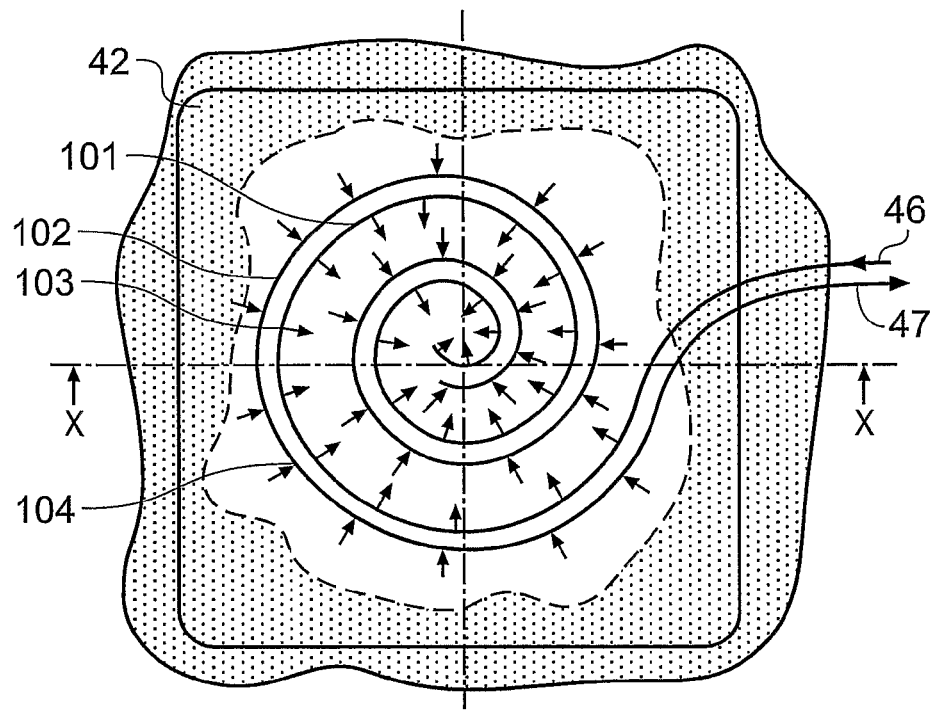
Figure 8B:
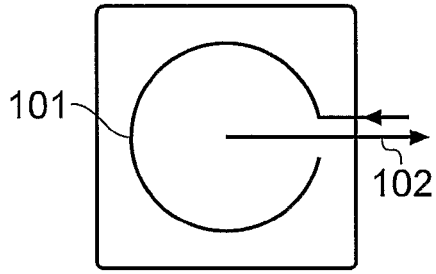
Figure 8C:
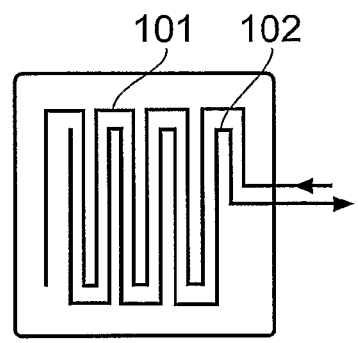
Figure 8D:
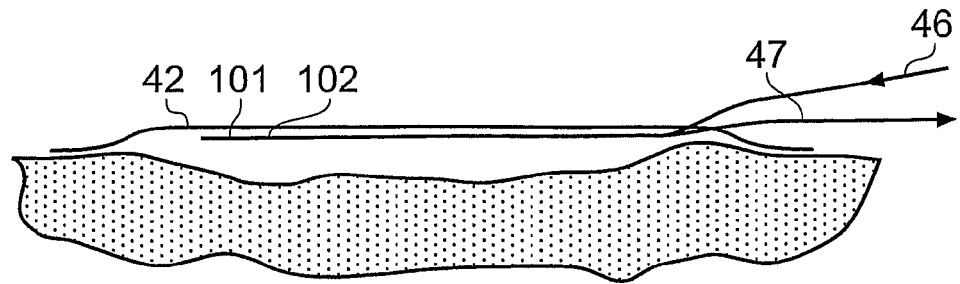
Figure 9A:
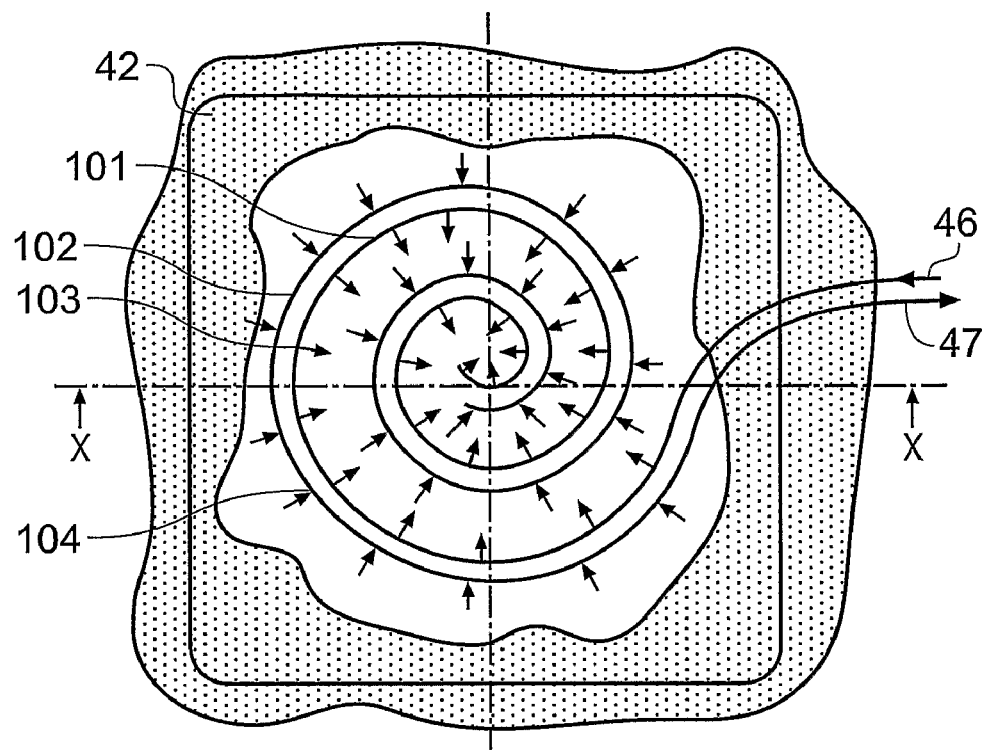
Figure 9B:
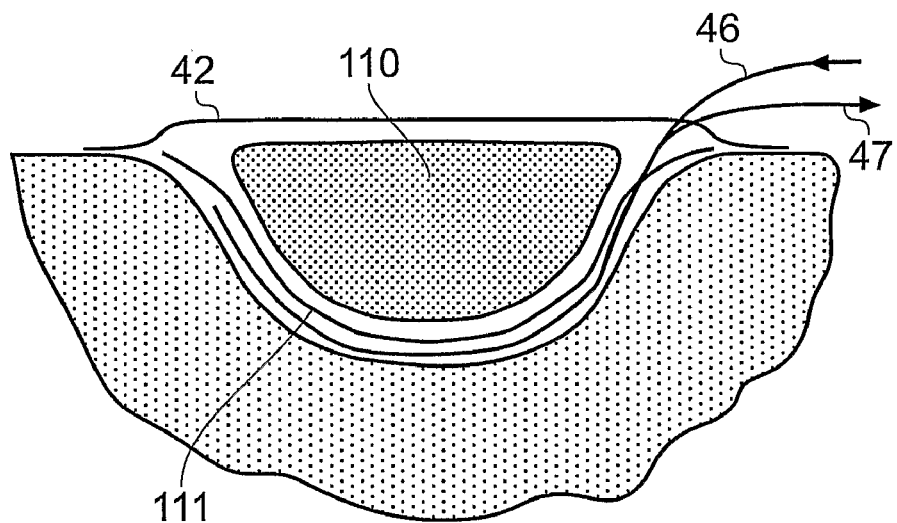

In FIGS. 8*a* and 8*d*, one layout of each of the pipes (101), (102) as inlet pipe and outlet pipe manifolds is a spiral.

In FIG. 8*b*, the layout is a variant of that of FIGS. 8*a* and 8*b*, with the layout of the inlet manifold (101) being a full or partial torus, and the outlet manifold (102) being a radial pipe.

Referring to FIG. 8*c*, there is shown another suitable layout in which the inlet manifold (101) and the outlet manifold (102) run alongside each other over the wound bed in a boustrophedic pattern, i.e. in the manner of ploughed furrows.

Referring to FIGS. 9*a* to 9*d*, there are shown other suitable layouts for deeper wounds, which are the same as shown in FIGS. 8*a* to 8*d*. The square backing layer (42) however has a wound filler (110) under, and may be permanently attached to, the backing layer (42), with an adhesive film (not shown) or by heat-sealing, which is an inverted hemispherical solid integer, here a resilient elastomeric foam, formed of a thermoplastic, preferably a cross-linked plastics foam.

Under the latter is a circular upwardly dished sheet (111) which conforms to, but is a separate structure, permanently unattached to, the solid filler (110). Through the sheet (111) pass the inlet pipe (46) and the outlet pipe (47), to run over the wound bed. These pipes (101), (102) again have a blind bore with orifices (103), (104) along the pipes (101), (102).

Alternatively (as in FIGS. 5*a* and 5*b*), where appropriate the dressing may be provided in a form in which the circular upwardly dished sheet (111) functions as the backing layer and the solid filler (110) sits on the sheet (42) as the backing layer, rather than under it. The filler (110) is held in place with an adhesive film or tape, instead of the backing layer (42).

In FIGS. 10*a* to 10*c*, inlet and outlet manifolds for the wound dressings for respectively delivering fluid to, and collecting fluid from, the wound, are formed by slots in and apertures through layers permanently attached to each other in a stack.

Thus, in FIG. 10*a* there is shown an exploded isometric view of an inlet manifold and outlet manifold stack (120) of five square coterminous thermoplastic polymer layers, being first to fifth layers (121) to (125), each attached with an adhesive film (not shown) or by heat-sealing to the adjacent layer in the stack (120).

The topmost (first) layer (121) (which is the most distal in the dressing in use) is a blank square capping layer.

The next (second) layer (122), shown in FIG. 10*b* out of the manifold stack (120), is a square layer, with an inlet manifold slot (126) through it. The slot (126) runs to one edge (127) of the layer (122) for connection to a mating end of a fluid inlet tube ((not shown), and spreads into four adjacent branches (128) in a parallel array with spaces therebetween.

The next (third) layer (123) is another square layer, with inlet manifold apertures (129) through the layer (123) in an array such that the apertures (129) are in register with the inlet manifold slot (126) through the second layer (122) (shown in FIG. 10*b*).

The next (fourth) layer (124), shown in FIG. 10*c* out of the manifold stack (120), is another square layer, with inlet manifold apertures (130) through the layer (124) in an array such that the apertures (130) are in register with the apertures (129) through the third layer (123).

It also has an outlet manifold slot (131) through it.

The slot (131) runs to one edge (132) of the layer (124) on the opposite side of the manifold stack (120) from the edge (127) of the layer (122), for connection to a mating end of a fluid outlet tube (not shown).

It spreads into three adjacent branches (133) in a parallel array in the spaces between the apertures (130) in the layer (124) and in register with the spaces between the apertures (129) in the layer (122).

The final (fifth) layer (125) is another square layer, with inlet manifold apertures (134) through the layer (125) in an array such that the apertures (134) are in register with the inlet manifold apertures (130) through the fourth layer (124) (in turn in register with the apertures (129) through the third layer (123). It also has outlet manifold apertures (135) in the layer (125) in an array such that the apertures (135) are in register with the outlet manifold slot (131) in the fourth layer (124).

It will be seen that, when the layers (121) to (125) are attached together to form the stack (120), the topmost (first) layer (121), the inlet manifold slot (126) through the second layer (122), and the third layer (123) cooperate to form an inlet manifold in the second layer (122), which is in use is connected to a mating end of a fluid inlet tube (not shown).

The inlet manifold slot (126) through the second layer (122), and the inlet manifold apertures (129), (130) and (134) through the layers (123), (124) and (125), all being mutually in register, cooperate to form inlet manifold conduits though the third to fifth layers (123), (124) and (125) between the inlet manifold in the second layer (122) and the proximal face (136) of the stack (120).

The third layer (121), the outlet manifold slot (131) through the fourth layer (124), and the fifth layer (125) cooperate to form an outlet manifold in the fourth layer (124), which is in use is connected to a mating end of a fluid outlet tube (not shown).

The outlet manifold slot (131) through the fourth layer (124), and the outlet manifold apertures (135) through the fifth layer (125), being mutually in register, cooperate to form outlet manifold conduits though the fifth layer (125) between the outlet manifold in the fourth layer (124) and the proximal face (136) of the stack (120).

Referring to FIG. 11, the apparatus (1) for aspirating, irrigating and/or cleansing wounds using cells or tissue is a variant of the apparatus (1) of FIG. 1.

It has bypass (711) around the pump (17), as a protection of the pump against any blockage in the system.

It is activated automatically by appropriate means, e.g. it is normally blocked by a bursting disc (not shown), or a pressure-activated motorised valve.

An alternative to the by-pass (711) is a pressure sensor in the system that will detect excessive load or pressure, and shut down the pump.

Referring to FIG. 12, the apparatus (1) for aspirating, irrigating and/or cleansing wounds using cells or tissue is a variant of the apparatus (1) of FIG. 2.

The latter is a two-phase system with a dialysis unit (21), but is one in which dialytic fluid passes only once across the surface of the dialytic membrane (28) in the first chamber (25) from a dialysate reservoir (not shown) to waste via a second bleed T-valve (36) into, e.g. a collection bag (not shown).

This variant has a dialysate recirculation tube (811) running between a first T-valve (816) on the inlet side of the dialysate pump (23) and a second T-valve (817) to permit the pump (23) to recirculate the dialysate once the circuit is primed in multiple passes through the dialysis unit (21).

The operation of the system will be apparent to the skilled person.

Figure 13A:
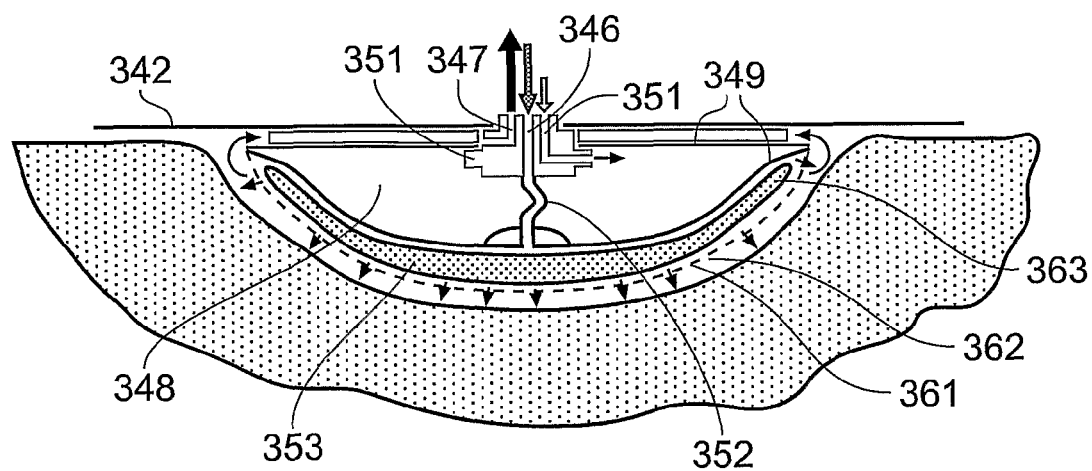
Figure 13B:
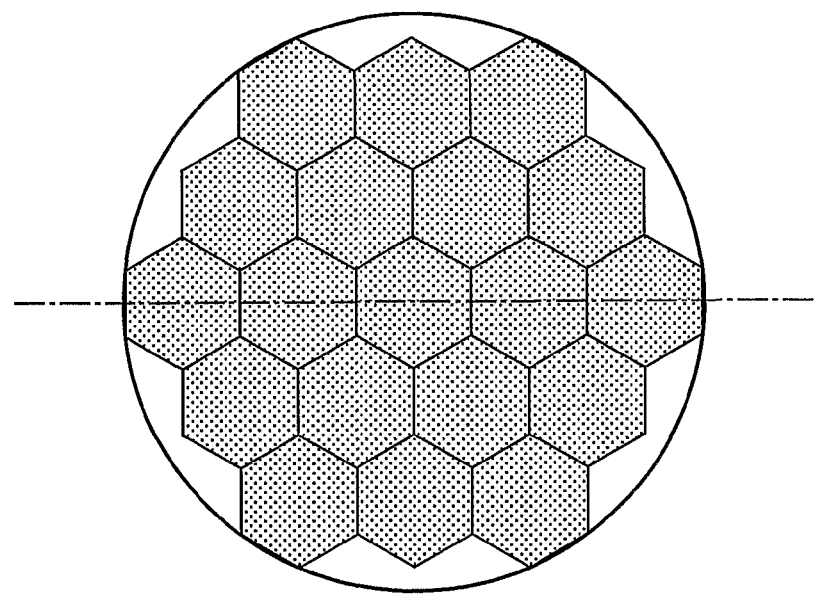
Figure 14:
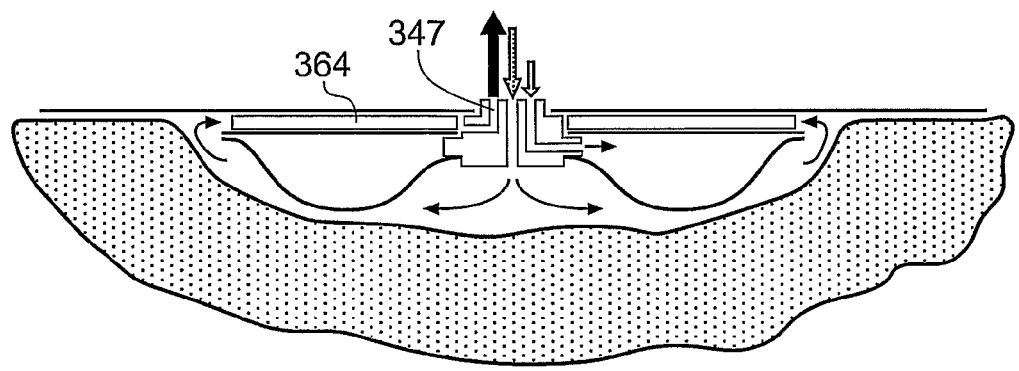
Figure 15:
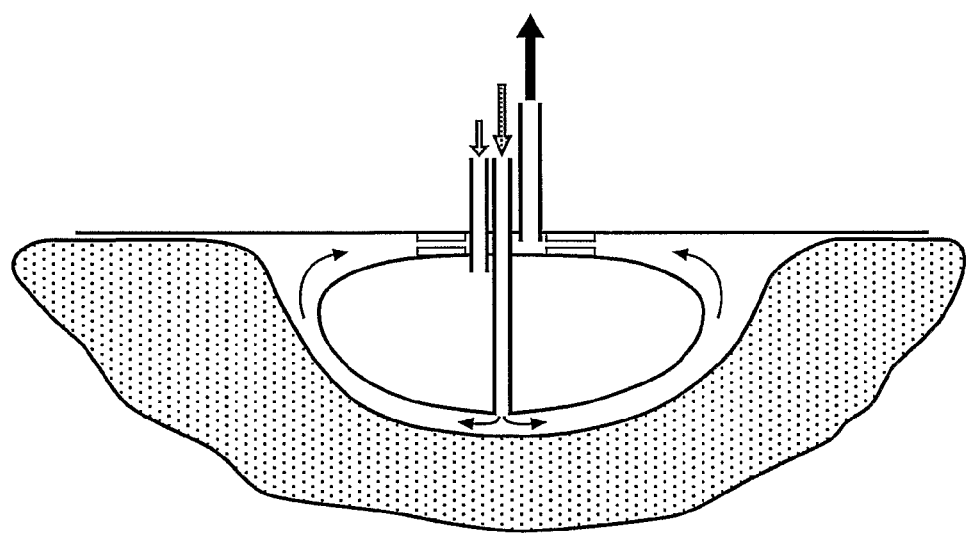

Referring to FIGS. 13 to 15, these forms of the dressing are provided with a wound filler (348) under a circular backing layer (342).

This comprises respectively a generally downwardly domed or toroidal, or oblately spheroidal conformable hollow body, defined by a membrane (349) which is filled with a fluid, here air or nitrogen, that urges it to the wound shape.

The filler (348) is permanently attached to the backing layer via a boss (351), which is e.g. heat-sealed to the backing layer (342).

An inflation inlet pipe (350), inlet pipe (346) and outlet pipe (347) are mounted centrally in the boss (351) in the backing layer (342) above the hollow body (348). The inflation inlet pipe (350) communicates with the interior of the hollow body (348), to permit inflation of the body (348). The inlet pipe (346) extends in a pipe (352) effectively through the hollow body (348). The outlet pipe (347) extends radially immediately under the backing layer (342).

In FIG. 13, the pipe (352) communicates with an inlet manifold (353), formed by a membrane (361) with apertures (362) that is permanently attached to the filler (348) by heat-sealing. It is filled with foam (363) formed of a suitable material, e.g. a resilient thermoplastic. Preferred materials include reticulated filtration polyurethane foams with small apertures or pores.

In FIG. 14, the outlet pipe (347) communicates with a layer of foam (364) formed of a suitable material, e.g. a resilient thermoplastic. Again, preferred materials include reticulated filtration polyurethane foams with small apertures or pores.

In all of FIGS. 13, 14 and 15, in use, the pipe (346) ends in one or more openings that deliver the irrigant fluid directly from the wound bed over an extended area.

Similarly, the outlet pipe (347) effectively collects the fluid radially from the wound periphery when the dressing is in use.

Figure 16A:
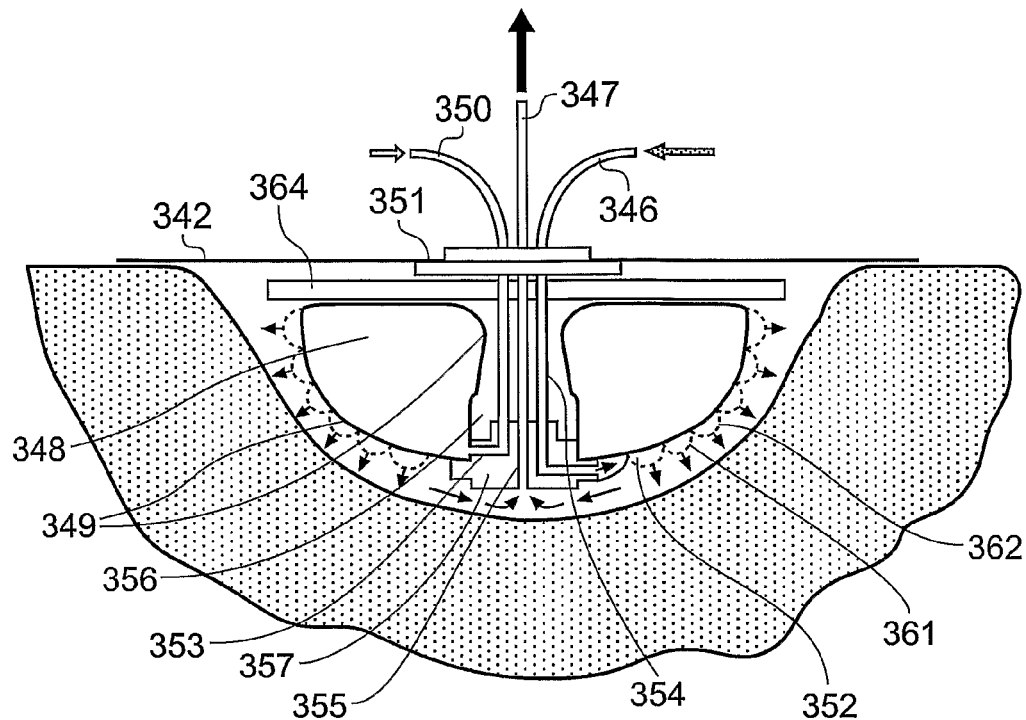
Figure 16B:
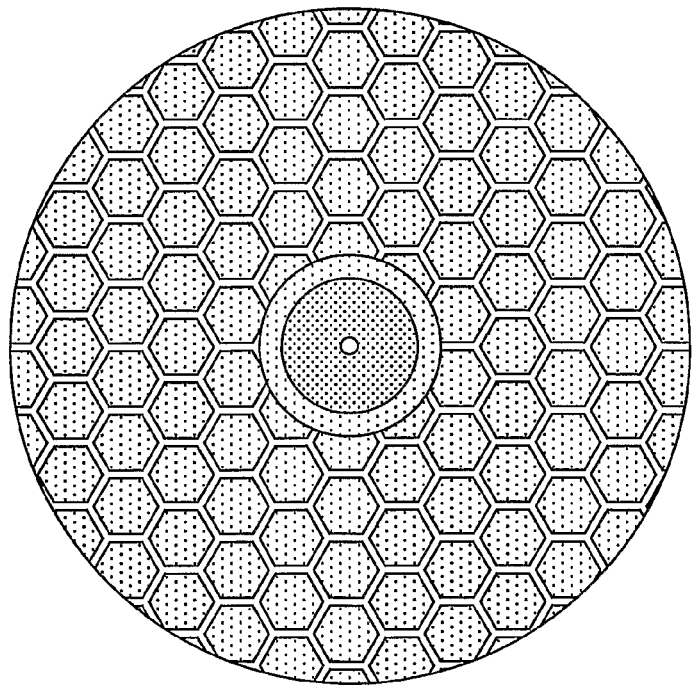

Referring to FIG. 16, the dressing is also provided with a wound filler (348) under a circular backing layer (342).

This also comprises a generally toroidal conformable hollow body, defined by a membrane (349) which is filled with a fluid, here air or nitrogen, that urges it to the wound shape.

The filler (348) may be permanently attached to the backing layer (342) via a first boss (351) and a layer of foam (364) formed of a suitable material, e.g. a resilient thermoplastic. Again, preferred materials include reticulated filtration polyurethane foams with small apertures or pores.

The first boss (351) and foam layer (364) are respectively heat-sealed to the backing layer (342) and the boss (351).

An inflation inlet pipe (350), inlet pipe (346) and outlet pipe (347) are mounted centrally in the first boss (351) in the backing layer (342) above the toroidal hollow body (348).

The inflation inlet pipe (350), inlet pipe (346) and outlet pipe (347) respectively each extend in a pipe (353), (354) and (355) through a central tunnel (356) in the hollow body (348) to a second boss (357) attached to the toroidal hollow body (348).

The pipe (353) communicates with the interior of the hollow body (348), to permit inflation of the body (348). The pipe (354) extends radially through the second boss (357) to communicate with an inlet manifold (352), formed by a membrane (361) that is permanently attached to the filler (348) by heat-sealing in the form of a reticulated honeycomb with openings (362) that deliver the irrigant fluid directly to the wound bed over an extended area. The pipe (355) collects the fluid flowing radially from the wound centre when the dressing is in use.

This form of the dressing is a more suitable layout for deeper wounds

Figure 17:
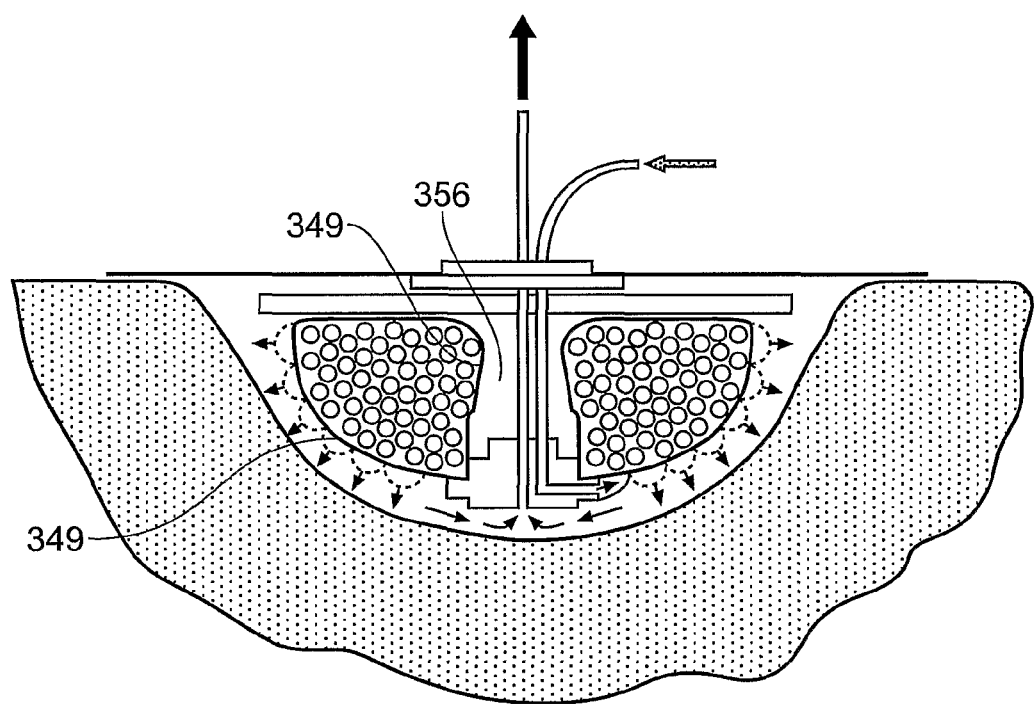

In FIG. 17, the dressing is similar to that of FIG. 16, except that the toroidal conformable hollow body, defined by a membrane (349), is filled with a fluid, here a solid particulates, such as plastics crumbs or beads, rather than a gas, such as air or an inert gas, such as nitrogen or argon, and the inflation inlet pipe (350) and pipe (353) are omitted from the central tunnel (356).

Examples of contents for the body (348) also include gels, such as silicone gels or preferably cellulosic gels, for example hydrophilic cross-linked cellulosic gels, such as Intrasite™ cross-linked materials. Examples also include aerosol foams, and set aerosol foams, e.g. CaviCare™ foam.

Figure 18A:
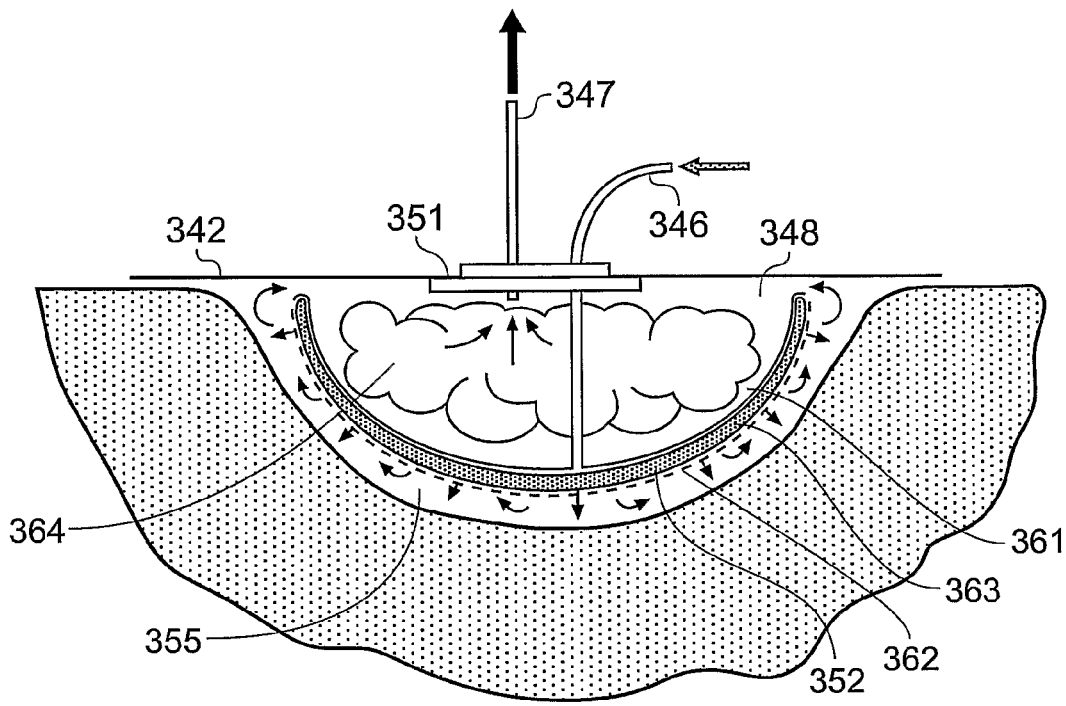
Figure 18B:
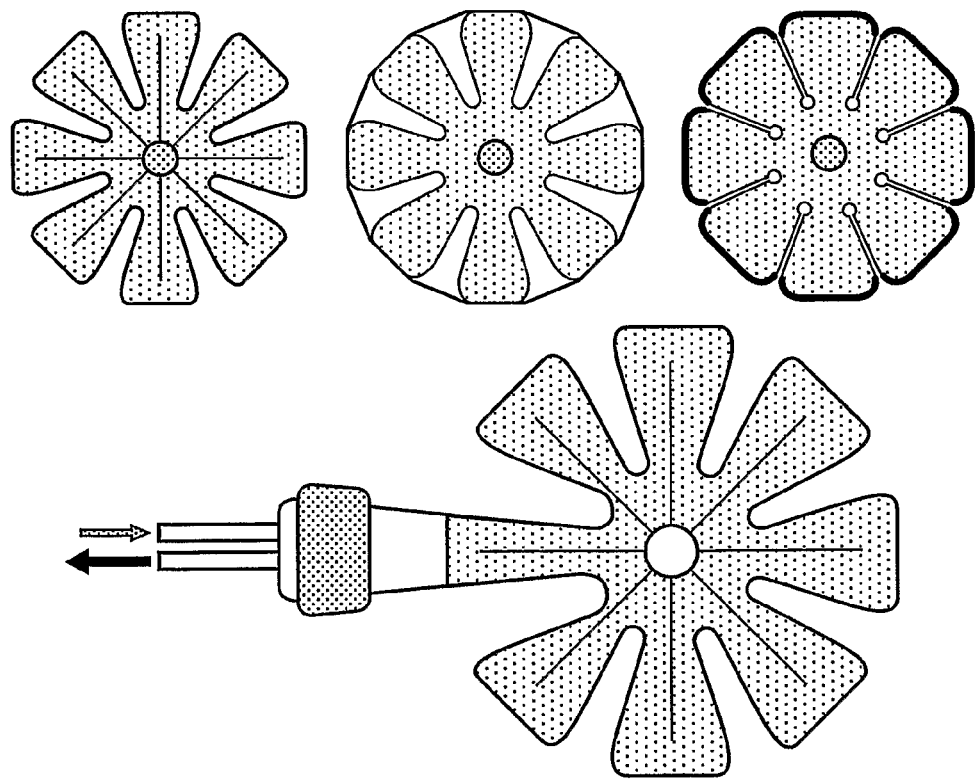
Figure 19:
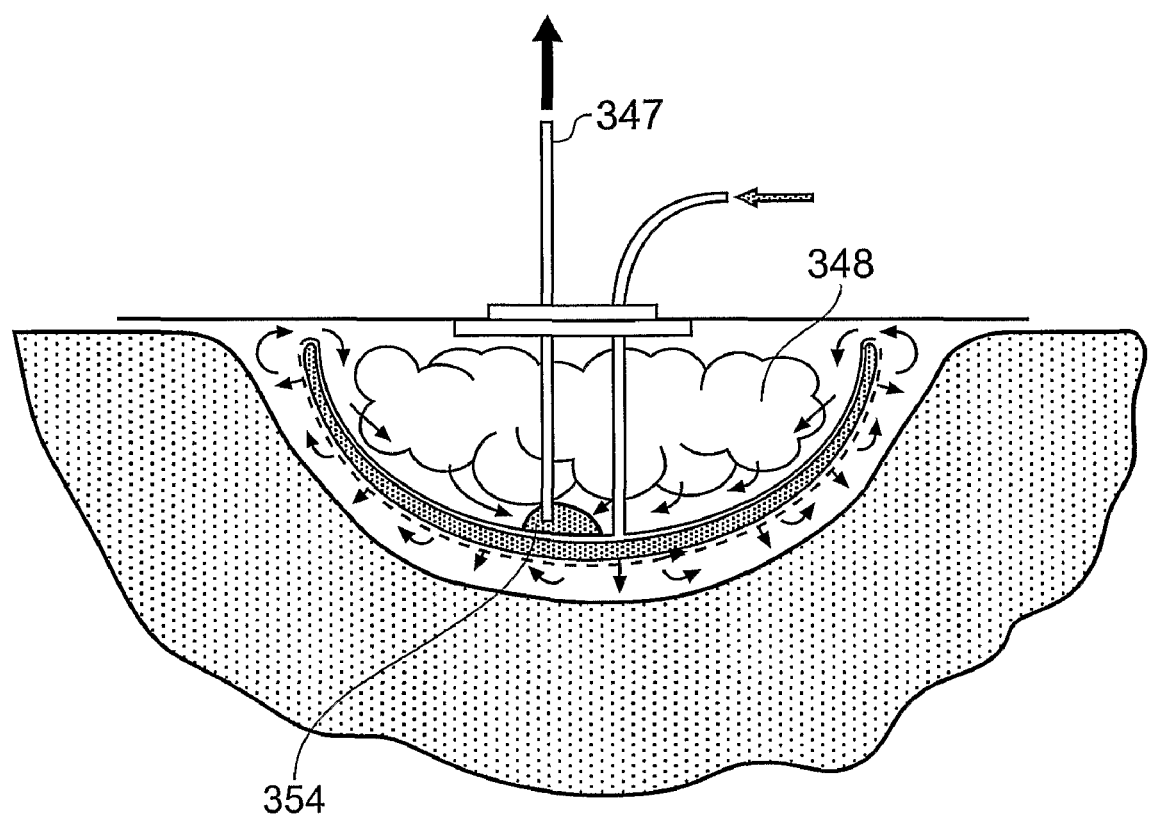

Referring to FIGS. 18 and 19, another form for deeper wounds is shown. This comprises a circular backing layer (342) and a chamber (363) in the form of a deeply indented disc much like a multiple Maltese cross or a stylised rose.

This is defined by an upper impervious membrane (361) and a lower porous film (362) with apertures (364) that deliver the irrigant fluid directly from the wound bed over an extended area. A number of configurations of the chamber (363) are shown, all of which are able to conform well to the wound bed by the arms closing in and possibly overlapping in insertion into the wound.

In a particular design of the chamber (363), shown lowermost, on of the arms extended and provided with an inlet port at the end of the extended arm. This provides the opportunity for coupling and decoupling the irrigant supply remote from the dressing and the wound in use.

An inlet pipe (346) and outlet pipe (347) are mounted centrally in a boss (351) in the backing layer (342) above the chamber (363). The inlet pipe (346) is permanently attached to, and communicate with the interior of, the chamber (363), which thus effectively forms an inlet manifold. The space above the chamber (363) is filled with a loose gauze packing (364).

In FIG. 18, the outlet pipe (347) collects the fluid from the interior of the dressing from just under the wound-facing face (343) of the backing layer (342).

A variant of the dressing of FIG. 18 is shown in FIG. 19. The outlet pipe (347) is mounted to open at the lowest point of the space above the chamber (363) into a piece of foam (374).

Figure 20:
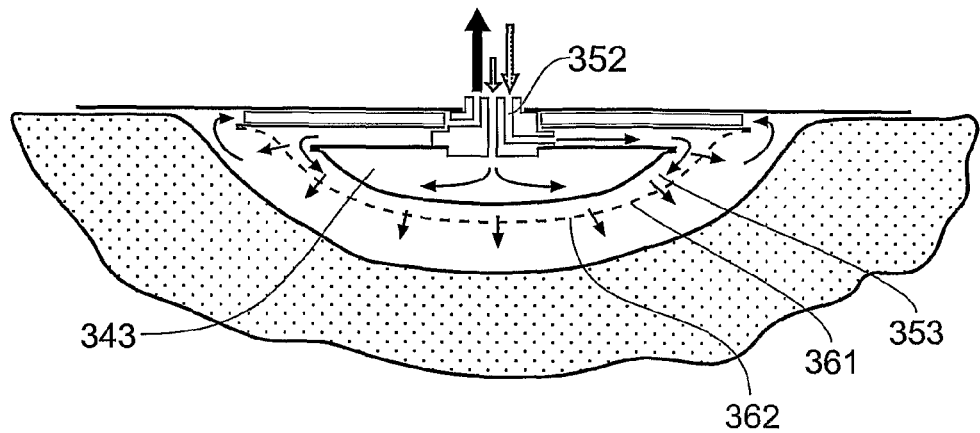

In FIG. 20, the dressing is similar to that of FIG. 13, except that the inlet pipe (352) communicates with an inlet manifold (353), formed by a membrane (361) with apertures (362), over the upper surface of the generally downwardly domed wound hollow filler (348), rather than through it.

Figure 22:
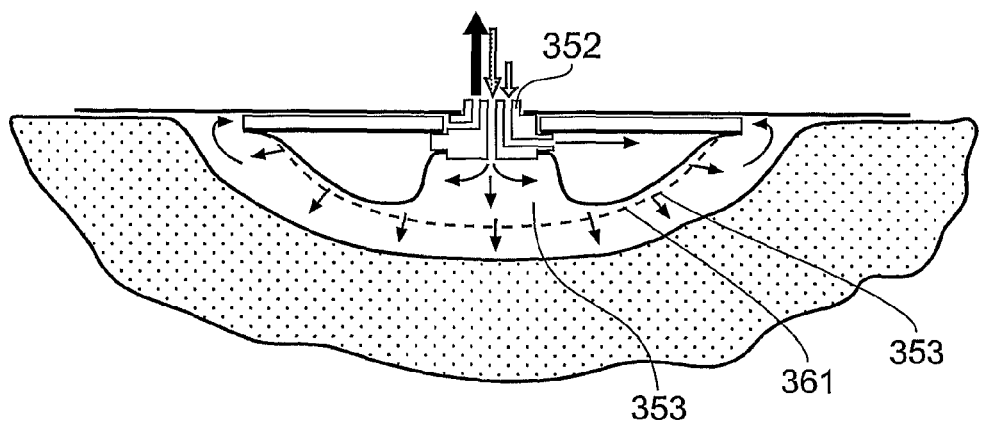

In FIG. 22, the dressing is similar to that of FIG. 14, with the addition of an inlet manifold (353), formed by a membrane (361) with apertures (362), over the lower surface of the generally downwardly domed annular wound hollow filler.

Figure 21:
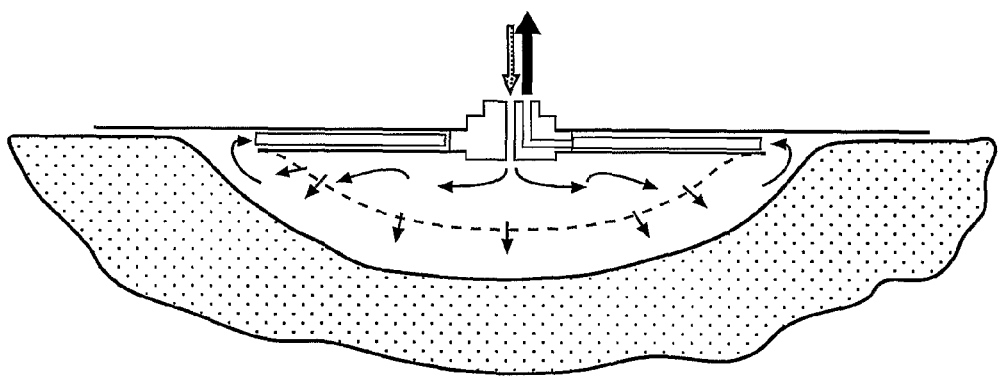

In FIG. 21, the generally downwardly domed annular wound hollow filler is omitted.

Figure 23:
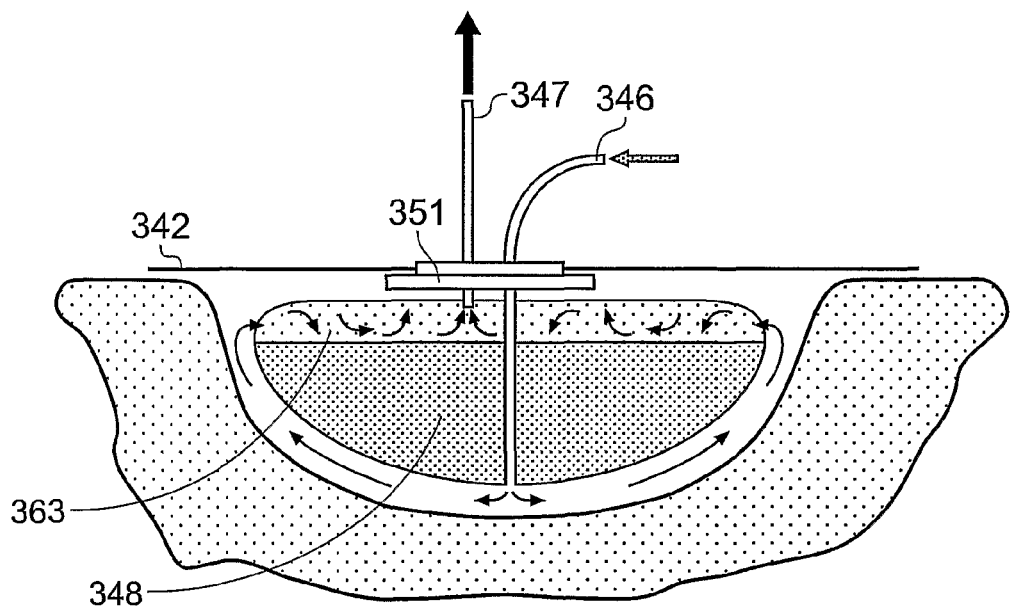

Referring to FIG. 23, another form for deeper wounds is shown. An inlet pipe (346) and outlet pipe (347) are mounted centrally in a boss (351) in the backing layer (342) above a sealed-off foam filler (348). The inlet pipe (346) is permanently attached to and passes through the filler (348) to the wound bed. The outlet pipe (347) is attached to and communicates with the interior of, a chamber (363) defined by a porous foam attached to the upper periphery of the filler (348). The chamber (363) thus effectively forms an outlet manifold.

Figure 24:
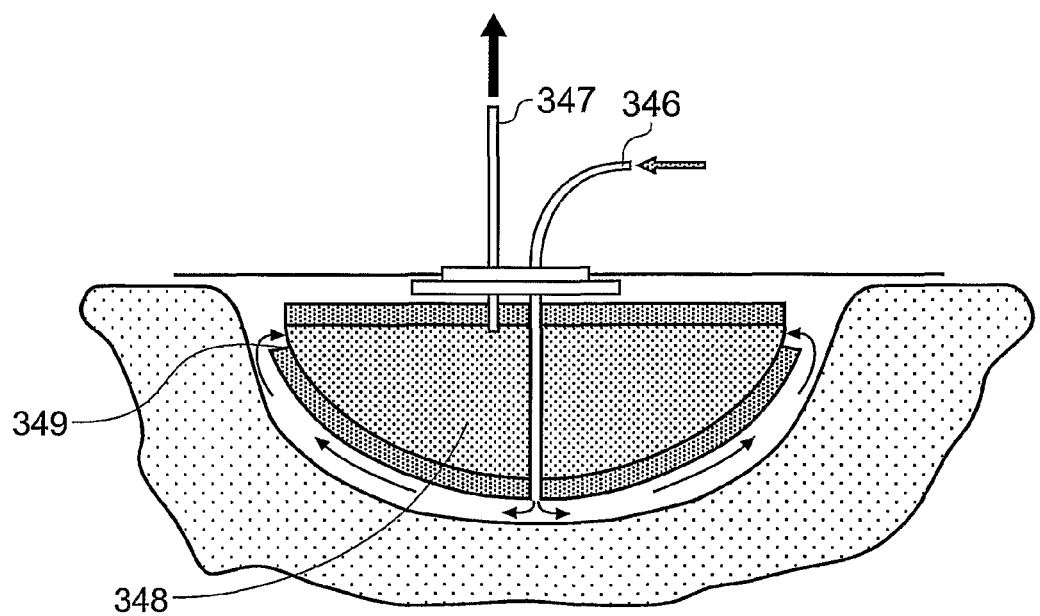

In FIG. 24, the foam filler (348) is only partially sealed-off. The inlet pipe (346) is permanently attached to and passes through the filler (348) to the wound bed. The outlet pipe (347) is attached to and communicates with the interior of the foam of the filler (348).

Fluid passes into an annular gap (349) near the upper periphery of the filler (348) into the foam, which thus effectively forms an outlet manifold.

Figure 25:
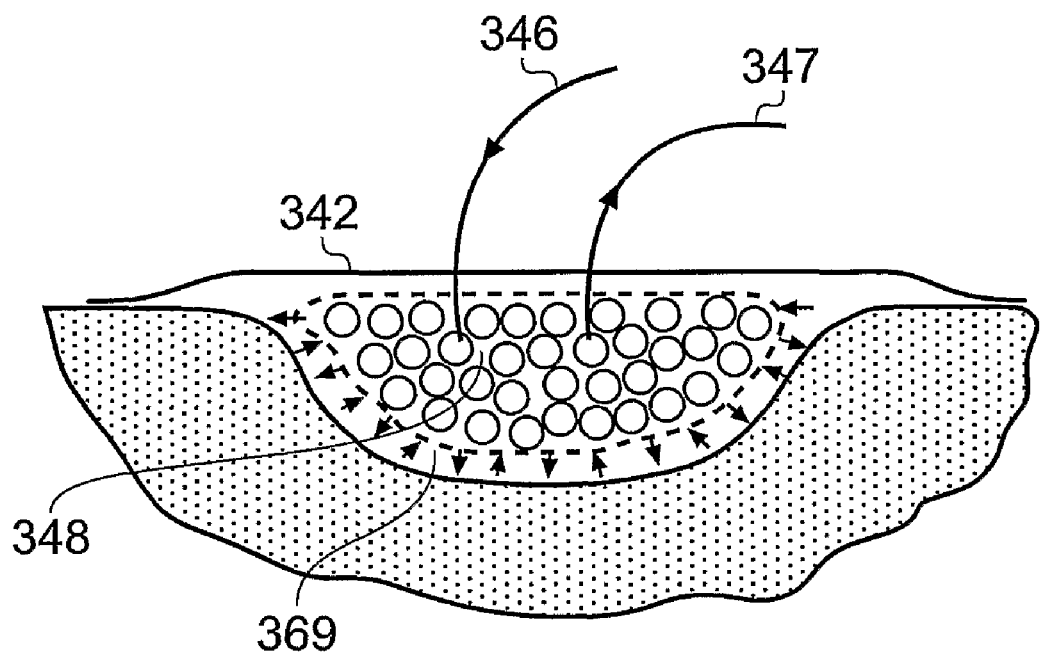
Figure 26:
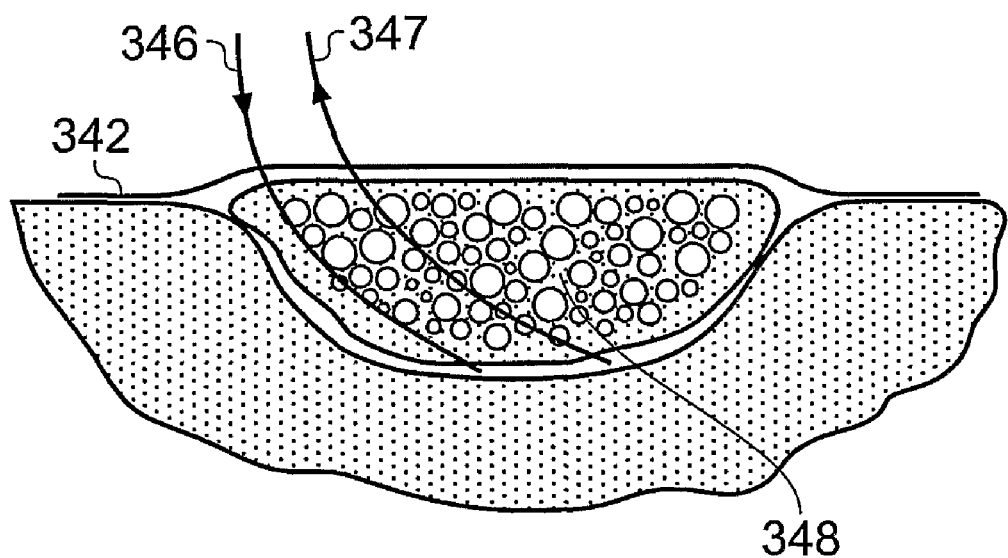

FIGS. 25 and 26 show dressings in which the inlet pipe (346) and outlet pipe (347) pass through the backing layer (342).

In FIG. 25, they communicate with the interior of a porous bag filler (348) defined by a porous film (369) and filled with elastically resilient plastics bead or crumb.

In FIG. 26, they communicate with the wound space just below a foam filler (348). The foam (348) may CaviCare™ foam, injected and formed in situ around the pipes (346) and (347).

Referring to FIG. 27, the apparatus (1) for aspirating, irrigating and/or cleansing wounds using cells or tissue is a major variant of the apparatus shown in FIG. 1.

The device for moving fluid through the wound and means for fluid cleansing using cells or tissue (17) in FIG. 1 is a peristaltic pump (18), e.g. preferably a small portable peristaltic pump, acting on the fluid circulation tube (13) downstream of the dressing (2) to apply a low negative pressure on the wound.

In the apparatus (1) shown in FIG. 27, the peristaltic pump (18) is replaced by:
a) a peristaltic pump, acting on the fluid supply tube (7) upstream of the dressing (2), and
b) a vacuum pump assembly with pressure regulating means, acting on the fluid circulation tube (13) downstream of the dressing (2),
to apply a low negative pressure on the wound.

The vacuum pump assembly comprises a tank (911) with an inlet tube (912) connecting to the fluid circulation tube (13) and communicating with the upper part of the tank (911), a waste tube (913) connecting to a waste pump (914) with waste bag (915) and communicating with the lower part of the tank (911),
a pump tube (916) connecting to a vacuum pump (918) and communicating with the upper part of the tank (911), and an outlet tube (917) connecting to the fluid circulation tube (13) to the means for cleansing using cells or tissue (17) and communicating with the lower part of the tank (911).

The vacuum pump (918) is controlled by a pressure feedback regulator (919) through an electrical line (920), the regulator receiving signals from a tank sensor (921) in the upper part of the tank (911), and a dressing sensor (922) in the wound space respectively via lines (923) and (924).

The operation of the apparatus (1) is similar to that of the apparatus in FIG. 1 mutatis mutandis.

The pressure feedback regulator (919) regulates the pressure at the wound and/or the tank (911).

If the amount of fluid in circulation becomes excessive, e.g. because the wound continues to exude heavily, the waste pump (914) may be started to transfer fluid from the lower part of the tank (911) to the waste bag (915).

The use of the apparatus of the present invention will now be described by way of example only in the following Examples:

EXAMPLE 1

To demonstrate the Benefit of Using Cells as a Cleanser in the Exudialysis Systems
Method
Cells
Human dermal fibroblasts (HS8/BS04) would be prepared for growth on Thermanox coverslips.
Media
Cells to be grown in DMEM media (Sigma, no. D6429) supplemented with 10% foetal calf serum; I-glutamine, non-essential amino acids and penicillin/streptomycin (various lot numbers). Media to be used in the experimental systems is supplemented with 5% (v/v) foetal calf serum and buffered with 1% (v/v) Buffer-All media (Sigma) to ensure stable pH of the media. Alternatively, cells will be grown in Eagle MEM media supplemented with 2 mM glutamate, 1.5 g/L sodium bicarbonate, 0.1 mM NEAA and 1 mM sodium pyruvate. The Eagle MEM media is the recommended media type for hepatocyte cell line.
Cells as Cleanser Aspect
Hepatocyte cell line (for example HepG2/C3A cell line; ATCC, ATCC-CRL-10741) would be used as the cells to remove factors deleterious to wound healing (e.g. hydrogen peroxide) from the media. The cell line would be grown either on a synthetic matrix (e.g. nylon mesh) or possibly a non-synthetic matrix and placed within the exudialysis system either enclosed in a dialysis type membrane or free floating in the media bottle.
Exudialysis System
A number of systems would be made up to provide the relevant controls and test conditions. These would include:

|  | Bottle 1 | Bottle 2 |
| --- | --- | --- |
| System 1 | Media | Media |
| System 2 | Media | Media and hepatocytes |
| System 3 | Media + catalase | Media |
| System 4 | Media + $H_2O_2$ | Media + hepatocytes |
| System 5 | Media + $H_2O_2$ | Media |

Equipment used in the flow system would include Ismatec IPC high precision peristaltic pumps with Ismatec pump tubing 1.02 mm ID and high strength silicon tubing (HS-0152-009, Cole Palmer Instruments) and hot plates.

H₂O₂

Hydrogen peroxide (Sigma, lot 074K3641; stock 8.8M, 30% soln) (250 µl) added to 21.75 ml DMEM/5% FCS media (or Eagle MEM media). 5.1 ml of the media added to 39.9 ml DMEM/5% FCS media and 5 ml of this was added to bottle 1 of the relevant systems giving a final concentration of 1.1 mM.

Catalase

Catalase is to be sued as a positive control. Snakeskin pleated dialysis tube (10 kDa MWCO; Pierce, no. 68100, lot EB9446) containing 15 ml catalase (or 86200 units; Sigma, C3155, lot 014K7029). The dialysis tubing was placed in Media bottle.

WST Assay

A WST assay would be used to measure the cells mitochondrial activity was on 6 coverslips from each system. WST reagent (Roche) is diluted to 10% v/v in experimental/BufferAll media. The coverslips are removed from the Minucell chamber and washed in 1 ml PBS. PBS was removed and 200 µWST/media added. The coverslips would then incubated at 37° C. for 45 min before transferring 150 µl of reagent to a 96 well plate. The absorbance at 450 nm with reference at 655 nm is determined using Ascent Multiskan Microtitre plate reader.

Results and Discussion

It would be expected that hepatocyte cells would convert and detoxify hydrogen peroxide to oxygen and water through the action of catalase, which is reported to be a protein component of hepatocytes. Through the detoxification action of hepatocytes, the fibroblasts present in the wound bed will survive and proliferate to a greater extent than to those exposed to hydrogen peroxide alone. Previous experiments have shown the presence of hydrogen peroxide kills the seeded fibroblasts (FIG. 29).

CONCLUSIONS

Hydrogen peroxide, at a sufficient concentration is toxic to fibroblast cells. A major role of hepatocytes is to detoxify biological fluids through enzymatic (e.g. catalase) mechanisms.

By placing hepatocyte cells within a flow system it would be expected that the hepatocytes would detoxify the media and remove hydrogen peroxide to a sufficient level to enable the fibroblasts present to survive and proliferate.

The invention claimed is:

1. An apparatus for aspirating, irrigating and/or cleansing wounds using cells or tissue, comprising
    a fluid flow path, comprising
        a wound dressing, having a backing layer and at least one inlet pipe for connection to a fluid supply tube, which passes through and/or under the backing layer, and at least one outlet pipe for connection to a fluid offtake tube, which passes through and/or under the backing layer, at least one inlet pipe being connected to a fluid recirculation tube, and at least one outlet pipe being connected to the fluid offtake tube; and
        a fluid cleanser component comprising cells or tissue, the fluid cleanser component having at least one inlet port connected to a fluid offtake tube of the fluid flow path and at least one outlet port connected to a fluid recirculation tube of the fluid flow path, the cells or tissue of the fluid cleanser component being configured to remove materials that are deleterious to wound healing from the fluid when the fluid is exposed to the cells or tissue;
        a fluid reservoir connected by a second fluid supply tube to an integer of the flow path; and
        a device for moving fluid through at least the wound dressing, the fluid cleanser component, and the fluid supply tube.

2. An apparatus as claimed in claim 1 in which the backing layer is capable of forming a relatively fluid tight seal or closure over a wound.

3. An apparatus as claimed in claim 1 in which the point at which the/or each inlet pipe and the/or each outlet pipe passes through and/or under the backing layer is capable of forming a relatively fluid-tight seal or closure over the wound.

4. An apparatus as claimed in claim 1 in which the wound dressing is a conformable wound dressing.

5. An apparatus as claimed in claim 1 in which the cells comprise hepatocytes.

6. An apparatus according to claim 1, in which the fluid cleanser component is a single-phase system, in which the circulating fluid from the wound passes through the fluid cleanser component and materials deleterious to wound healing are removed, without the circulating fluid coming into direct or indirect contact with another fluid in the fluid cleanser component.

7. An apparatus according to claim 1, in which the fluid cleanser component is a two-phase system, in which the circulating fluid from the wound passes through the fluid cleanser component and materials deleterious to wound healing are removed by the circulating fluid coming into direct or indirect contact with another fluid in the fluid cleanser component.

8. An apparatus according to claim 7, in which the fluid cleanser component, the circulating fluid from the wound and the other fluid in the fluid cleanser component are separated by an integer which is selectively permeable to materials deleterious to wound healing.

9. An apparatus according to claim 7, in which the fluid cleanser component, the circulating fluid from the wound and the other fluid in the fluid cleanser component are separated by an integer which is not selectively permeable to materials deleterious to wound healing, and the other fluid comprises and/or is in contact with a material that removes materials deleterious to wound healing.

10. An apparatus according to claim 1, wherein the materials deleterious to wound healing are oxidants; proteases; endotoxins; autoinducer signalling molecules; inhibitors of angiogenesis; pro-inflammatory cytokine; and inflammatories.

11. An apparatus according to claim 1 further comprising one or more devices to aspirate and irrigate the wound, such that irrigant fluid may be supplied to fill the flowpath from the fluid reservoir via the second fluid supply tube while aspirate fluid is aspirated by one of said one or more devices through the fluid offtake.

12. An apparatus according to claim 11 wherein the one or more devices to aspirate and irrigate the wound comprises
    a) a first device for moving fluid through the wound applied to fluid downstream of and away from the wound dressing, and
    b) a second device for moving fluid through the wound applied to the irrigant in the fluid supply tube upstream of and towards the wound dressing.

13. An apparatus according to claim 12 in which the first device and/or second device is a fixed throughput device and the one or more devices to aspirate and irrigate the wound also comprises at least one of means for supply flow regulation, connected to a fluid supply tube, and means for aspirate flow regulation, connected to a fluid offtake tube.

14. The apparatus of claim 1 wherein the device for moving fluid through the wound is a diaphragm pump or a peristaltic pump.

15. The apparatus of claim 1 in which the flow rate is a varied flow rate, either randomly or regularly cyclical.

16. The apparatus of claim 15 wherein the regular or random cycles of flow rate have a frequency of up to 48 per 24 hours.

17. The apparatus of claim 15 wherein the pulses of flow velocity have a frequency of from 1 to 60 per min.

18. The apparatus of claim 14 wherein the device for moving fluid across the wound enables the flow to be a parallel flow, radial streaming, spiral streaming, helical streaming, spirohelical streaming or circular streaming.

19. An apparatus according to claim 11 in which the one or more devices to aspirate and irrigate the wound comprises a suction source for creating a negative pressure beneath the backing layer.

20. An apparatus according to claim 19 in which the negative pressure is between about 1.01 and 100.3 kPa (0.01 and 0.99 atmospheres).

21. An apparatus as claimed in claim 1 in which the backing layer is semi-permeable to allow a flow rate of gas through it.

22. An apparatus as claimed in claim 1 in which the apparatus comprises a wound contact layer.

23. An apparatus as claimed in claim 22 in which the wound contact layer comprises a material chosen from the group: gauze, foam, a porous material, semi-porous material, semi-permeable material, an elastic filler, and an inflatable filler.

24. An apparatus as claimed in claim 1 in which the apparatus is portable.

25. An apparatus as claimed in claim 1 which the cells or tissue are bound or retained on an insoluble substrate over and/or through which a fluid flowing through the fluid cleanser component passes.

26. The apparatus of claim 11 in which the apparatus is configured to provide either sequential or simultaneous aspiration and irrigation.

27. An apparatus for aspirating, irrigating and/or cleansing wounds using cells or tissue, comprising:
  a wound dressing having a backing layer and at least one inlet pipe for connection to a fluid supply tube in communication with a space between the backing layer and the wound,
  at least one inlet pipe being connected to a fluid recirculation tube, and at least one outlet pipe being connected to a fluid offtake tube;
  a fluid cleanser component comprising a tissue component, the fluid cleanser component having at least one inlet port connected to the fluid offtake tube and at least one outlet port connected to a fluid recirculation tube, the tissue component being configured to remove materials that are deleterious to wound healing from the fluid or to modify the cellular elements of the wound bed through biochemical, enzymatic or physical means by the elaboration or the uptake of materials or the combination of both elaboration and uptake; and
  a device for moving fluid through at least the wound dressing, the fluid cleanser component, and the fluid supply tube.

28. An apparatus as claimed in claim 27 in which the fluid cleanser component is a single-phase system in which fluid from the wound passes through the fluid cleanser component and materials deleterious to wound healing are removed without the fluid from the wound coming into direct or indirect contact with another fluid in the fluid cleanser component.

29. An apparatus as claimed in claim 27 in which the fluid cleanser component is a two-phase system in which fluid from the wound passes through the fluid cleanser component and materials deleterious to wound healing are removed by the fluid from the wound coming into direct or indirect contact with another fluid in the fluid cleanser component.

30. An apparatus as claimed in claim 27 further comprising one or more devices to aspirate and irrigate the wound, such that irrigant fluid may be supplied to fill the flowpath from the fluid reservoir via the second fluid supply tube while aspirate fluid is aspirated by a device through the fluid offtake.

31. An apparatus according to claim 30 in which the one or more devices to aspirate and irrigate the wound comprises:
  a) a first device for moving fluid through the wound applied to fluid downstream of and away from the wound dressing, and
  b) a second device for moving fluid through the wound applied to the irrigant in the fluid supply tube upstream of and towards the wound dressing.

32. An apparatus according to claim 31 in which the first device and/or second device is a fixed throughput device and the one or more devices to aspirate and irrigate the wound also comprises at least one of means for supply flow regulation connected to a fluid supply tube and means for aspirate flow regulation connected to a fluid offtake tube.

33. An apparatus according to claim 27 further comprising a source of negative pressure for the wound.

34. The apparatus of claim 27 wherein the device for moving fluid through the wound is a diaphragm pump or a peristaltic pump.

35. The apparatus of claim 27 in which a rate of flow of fluid through the dressing varied, either randomly or regularly cyclical.

36. An apparatus for aspirating, irrigating and/or cleansing wounds using cells or tissue, comprising:
  a fluid flow path, comprising
    a wound dressing, having a backing layer and at least one inlet pipe for connection to a fluid supply tube, which passes through and/or under the backing layer, and at least one outlet pipe for connection to a fluid offtake tube, which passes through and/or under the backing layer, at least one inlet pipe being connected to a fluid recirculation tube, and at least one outlet pipe being connected to the fluid offtake tube; and
    a fluid cleanser comprising a chamber having cells or tissue contained therein, the chamber having at least one inlet port connected to a fluid offtake tube and at least one outlet port connected to a fluid recirculation tube, the cells or tissue being configured to remove materials that are deleterious to wound healing from the fluid;
  a fluid reservoir connected by a second fluid supply tube to an integer of the flow path; and
  a device for moving fluid through at least the wound dressing, the fluid cleanser, and the fluid supply tube.

37. An apparatus as claimed in claim 36 in which the fluid cleanser component is a single-phase system in which fluid from the wound passes through the fluid cleanser component and materials deleterious to wound healing are removed without the fluid from the wound coming into direct or indirect contact with another fluid in the fluid cleanser component.

38. An apparatus as claimed in claim 36 in which the fluid cleanser component is a two-phase system in which fluid from the wound passes through the fluid cleanser component and materials deleterious to wound healing are removed by the fluid from the wound coming into direct or indirect contact with another fluid in the fluid cleanser component.

39. An apparatus as claimed in claim 36 further comprising one or more devices to aspirate and irrigate the wound, such that irrigant fluid may be supplied to fill the flowpath from the fluid reservoir via the second fluid supply tube while aspirate fluid is aspirated by a device through the fluid offtake.

40. An apparatus according to claim 39 in which the one or more devices to aspirate and irrigate the wound comprises:
   a) a first device for moving fluid through the wound applied to fluid downstream of and away from the wound dressing, and
   b) a second device for moving fluid through the wound applied to the irrigant in the fluid supply tube upstream of and towards the wound dressing.

41. An apparatus according to claim 40 in which the first device and/or second device is a fixed throughput device and the one or more devices to aspirate and irrigate the wound also comprises at least one of means for supply flow regulation, connected to a fluid supply tube, and means for aspirate flow regulation, connected to a fluid offtake tube.

42. An apparatus according to claim 36 further comprising a source of negative pressure for the wound.

43. The apparatus of claim 36 wherein the device for moving fluid through the wound is a diaphragm pump or a peristaltic pump.

44. The apparatus of claim 36 in which a rate of flow of fluid through the dressing varied, either randomly or regularly cyclical.

* * * * *